US009890404B2

(12) United States Patent
Choi et al.

(10) Patent No.: US 9,890,404 B2
(45) **Date of Patent: *Feb. 13, 2018**

(54) MICROORGANISMS FOR PRODUCING PUTRESCINE AND METHOD FOR PRODUCING PUTRESCINE USING SAME

(75) Inventors: Hyang Choi, Anyang-si (KR); Kyoung Min Lee, Daejeon (KR); Min Sun Kang, Yeosu-si (KR); Sung Hoo Jhon, Seoul (KR); Hye Won Um, Suwon-si (KR); Su Jin Choi, Daegu (KR); Han Won Lee, Seoul (KR); Soo An Shin, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 63 days.

This patent is subject to a terminal disclaimer.

(21) Appl. No.: 13/992,242

(22) PCT Filed: Dec. 8, 2011

(86) PCT No.: PCT/KR2011/009478

§ 371 (c)(1), (2), (4) Date: Jun. 6, 2013

(87) PCT Pub. No.: WO2012/077995

PCT Pub. Date: Jun. 14, 2012

(65) Prior Publication Data

US 2014/0004577 A1 Jan. 2, 2014

(30) Foreign Application Priority Data

Dec. 8, 2010 (KR) ........................ 10-2010-0124867
Dec. 7, 2011 (KR) ........................ 10-2011-0130595

(51) Int. Cl.

| | |
|---|---|
| ***C12P 13/00*** | (2006.01) |
| ***C12N 15/77*** | (2006.01) |
| ***C07K 14/34*** | (2006.01) |
| ***C12N 9/02*** | (2006.01) |
| ***C12N 9/10*** | (2006.01) |
| ***C12N 9/12*** | (2006.01) |
| ***C12N 9/88*** | (2006.01) |
| ***C12R 1/15*** | (2006.01) |

(52) U.S. Cl.

CPC ............ *C12P 13/001* (2013.01); *C07K 14/34* (2013.01); *C12N 9/0008* (2013.01); *C12N 9/1018* (2013.01); *C12N 9/1029* (2013.01); *C12N 9/1096* (2013.01); *C12N 9/1217* (2013.01); *C12N 9/88* (2013.01); *C12R 1/15* (2013.01); *C12Y 102/01038* (2013.01); *C12Y 201/03003* (2013.01); *C12Y 203/01035* (2013.01); *C12Y 206/01013* (2013.01); *C12Y 207/02008* (2013.01); *C12Y 401/01017* (2013.01)

(58) Field of Classification Search

CPC .... C07K 14/34; C12N 9/0008; C12N 9/1018; C12N 9/1029; C12N 9/1096; C12N 9/1217; C12N 9/88; C12P 13/001; C12Y 102/01038; C12Y 201/03003; C12Y 203/01035; C12Y 206/01013; C12Y 207/02008; C12Y 401/01017

See application file for complete search history.

(56) References Cited

U.S. PATENT DOCUMENTS

2010/0203599 A1 8/2010 Lee et al.

FOREIGN PATENT DOCUMENTS

| | | |
|---|---|---|
| JP | 2007097573 A | 4/2007 |
| JP | 2014-500728 A | 1/2014 |
| WO | 2006/005603 A1 | 1/2006 |

OTHER PUBLICATIONS

Schneider et al., Appl. Microbiol. Biotechnol. 88:859-868, Jul. 27, 2010.*
Nakamura et al., Applied and Environmental Microbiology 73(14):4491-4498, 2007.*
Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Zhou et al., Cell Mol Life Sci 63(19-20):2260-2290, 2006.*
Kozak, M., Gene 234:187-208, 1999.*
Hwang, Joong-Hee, et al., "Effect of Increased Glutamate Availability on L-Ornithine Production in Corynebacterium glutamicum," J. Microbiol. Biotechnol. 18(4): 704-710, 2008.
Qian et al., "Metabolic Engineering of *Escherichia coli* for the Production of Putrescine: A Four Carbon Diamine," Biotechnology Bioengineering 104: 651-662, 2009.
Barroso et al., Database UniProtKB/Swiss-Prot, Accession No. P21169, Accessed Nov. 2, 2010, two pages.
Shun and Lee, "Cloning of the argF Gene Encoding the Ornithine Carbamoyltransferase from Corynebacterium jlutamicurn," Md. Cells. 9(3): 333-337, 1999.

* cited by examiner

*Primary Examiner* — Delia Ramirez

(57) ABSTRACT

The present invention relates to a putrescine-producing microorganism and a method for producing putrescine using the same. To be more specific, the present invention is directed to a microorganism given the ability to produce putrescine which is generated by blocking a biosynthetic pathway from ornithine to arginine, increasing the intracellular level of glutamate, enhancing the biosynthetic pathway of ornithine from glutamate, and introducing extracellular ornithine decarboxylase; and a method for producing putrescine by using the microorganism.

7 Claims, 3 Drawing Sheets

[Figure 1]
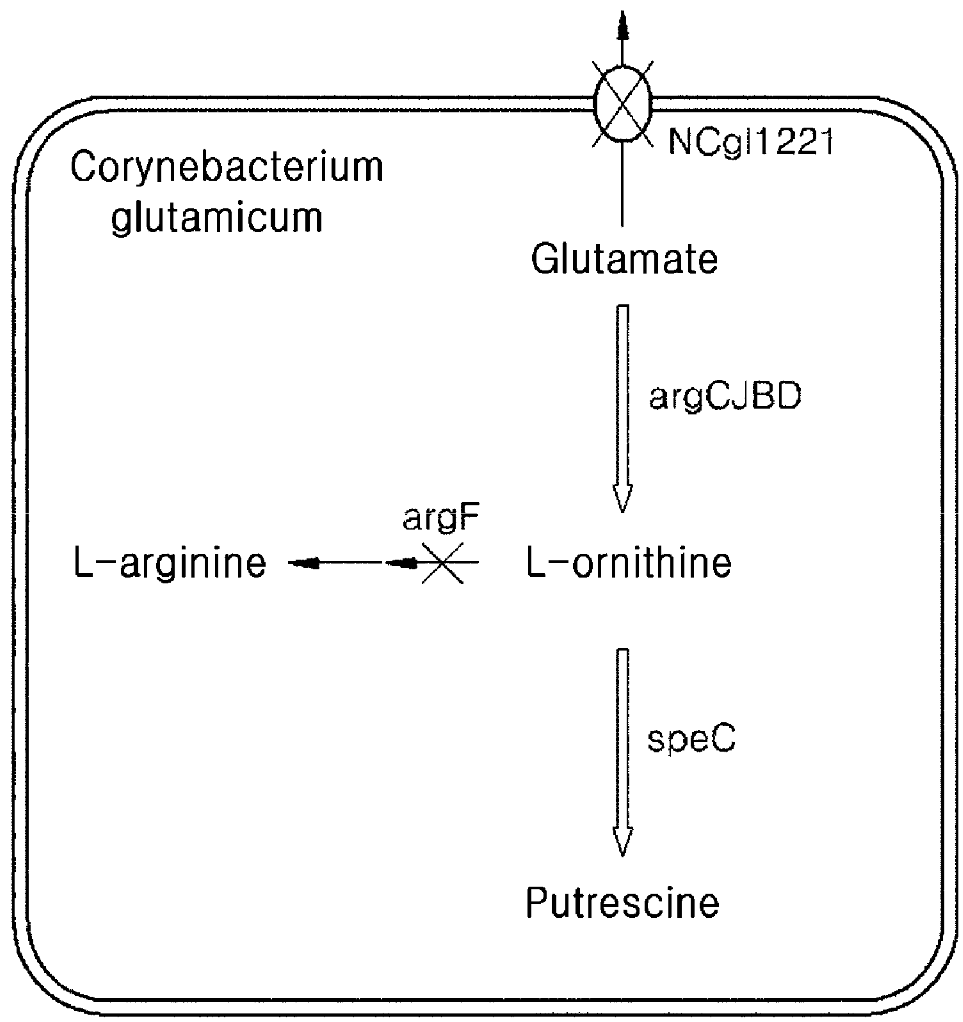

[Figure 2]
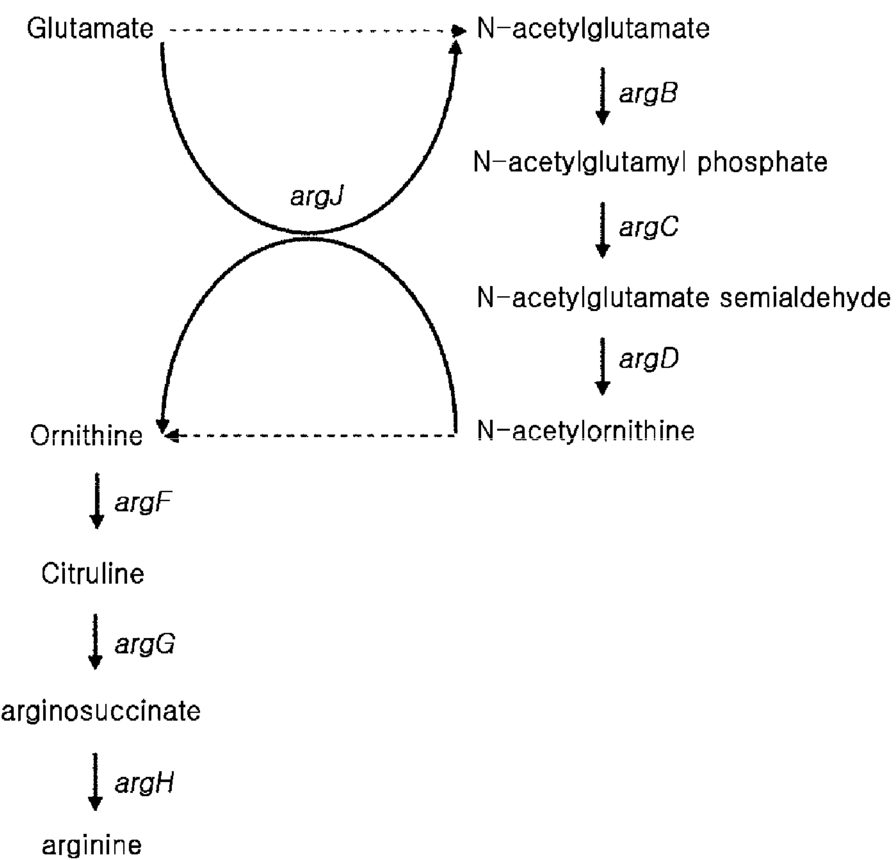

[Figure 3]
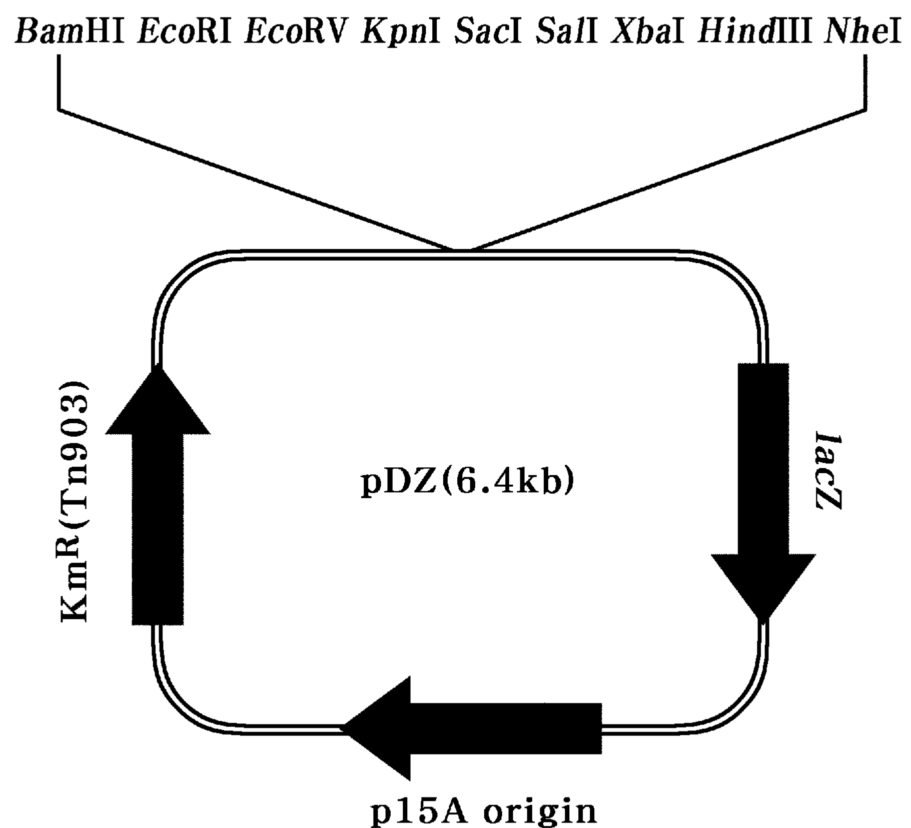

MICROORGANISMS FOR PRODUCING PUTRESCINE AND METHOD FOR PRODUCING PUTRESCINE USING SAME

CROSS-REFERENCES TO RELATED APPLICATIONS

This application is a U.S. national phase application of International PCT Patent Application No. PCT/KR2011/009478, which was filed on Dec. 8, 2011, which claims priority to Korean Patent Application Nos. 10-2011-0130595, filed Dec. 7, 2011 and 10-2010-0124867, filed Dec. 8, 2010. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_023_00US_ST25.txt. The text file is 50 KB, was created on, Sep. 9, 2013, and is being submitted electronically via EFS-Web.

TECHNICAL FIELD

The present invention relates to a putrescine-producing microorganism and a method for producing putrescine using the same.

BACKGROUND ART

Polyamine is a substance present in most of the living cells. Spermidine or spermine belonging to polyamine is found in various species such as bacteria, fungus, and animals. Putrescine or 1,4-butanediamine which is a precursor in spermidine and spermine metabolism is found in a gram-negative bacteria or fungus, and it is present in wide range of concentration in various species suggesting that it has an important role in metabolic pathway.

Putrescine is a building block in a synthesis of polyamine nylon-4, 6 which is produced by reacting putrescine with adipic acid. To be used in manufacture of a processed plastic as a raw material, putrescine is usually produced by chemical synthesis involving conversion of propylene to acrylonitrile and to succinonitrile. This chemical synthesis consists of three-step process comprising catalytic oxidation reaction which consumes a lot of energy, reaction using a toxic chemical such as cyanide, and hydrogenation reaction that uses high-pressure hydrogen. Production of putrescine by chemical synthesis is not environmentally friendly and also consumes a lot of energy leading to depletion of petroleum resource. Therefore, a more environmentally friendly and energy-effective method involving biomass utilization needs to be developed for putrescine production.

In microorganism, a biosynthetic pathway of putrescine is the same as L-arginine biosynthetic pathway from glutamate to ornithine synthesis step. Putrescine can be synthesized by two pathways such as ornithine decarboxylation or arginine decarboxylation. These two pathways produce the energy required for metabolism or allow the cell to have resistance to oxidative stress. A method for production of putrescine at a high concentration by transformation of *E. coli* and *Corynebacterium* has been reported. Production of putrescine in *E. coli* can be achieved by increasing expression level of ornithine decarboxylase and glutamate acetyltransferase. Also, putrescine can be produced at high concentration by removing spermidine and acetylputrescine synthetic pathways which degrade or utilize putrescine (Qian. Z D. et al., Biotechnol. Bioeng. 104:4, 651-662, 2009, International Patent Publication No. WO06/005603. International Patent Publication No. WO09/125924). Meanwhile, in *Corynebacterium* sp. strain which lacks putrescine synthetic pathway, putrescine may be produced from ornithine through insertion of ornithine decarboxylase gene derived from *E. coli* or putrescine may be produced from L-arginine by insertion of the gene of L-arginine decarboxylase and agamatinase derived from *E. coli*. Ornithine pathway actually can produce about 50 times higher amount of putrescine than L-arginine pathway (Schneider et al., Appl. Microbiol. Biotechnol. 88:4, 859-868, 2010).

Meanwhile, it was found that *E. coli* can grow normal in the presence of 44 g/L putrescine, while *Corynebacterium glutamicum* can grow normal in the presence of 66 g/L putrescine. Therefore, it seems more effective to use *Corynebacterium* sp. strain which can survive at higher concentration of putrescine than *E. coli* in development of microorganism for producing putrescine.

*Corynebacterium* sp. strains are commercially applicable microorganism that is widely used in production of amino acid, nucleic acids, enzymes, and antibiotic analogs. In *Corynebacterium* sp. strain, L-arginine is synthesized from glutamate by enzymes expressed from the gene of arginine operon composed of argCJBDFRGH. Arginine operon genes that take the most important role in biosynthesis of L-arginine uses intracellularly synthesized L-glutamate as a substrate for arginine synthesis. FIG. 2 shows a schematic diagram of a synthetic pathway of arginine from glutamate in *Corynebacterium* sp. strain. In arginine synthetic pathway, ArgJ converts glutamate to N-acetylglutamate, ArgB converts N-acetylglutamate to N-acetylglutamyl phosphate, ArgC converts N-acetylglutamyl phosphate to N-acetylglutamate semialdehyde, ArgD converts N-acetylglutamate semialdehyde to N-acetylornithine, ArgJ converts N-acetylornithine to ornithine, ArgF converts ornithinie to L-citrulline, ArgG converts L-citrulline to argininosuccinate, and ArgH converts argininosuccinate to arginine.

Previously known arginine-producing strains were developed by increasing the expression level of enzyme involved in arginine biosynthesis through introducing mutation to arginine operon or mutating promoter. Among the genes in arginine operon, argR which regulates and suppresses the expression of arginine operon gene and argB which is inhibited by arginine concentration have been targeted in many studies to increase arginine production level (Korea Patent Publication No. 2010-0060909).

Putrescine biosynthetic pathway is the same as arginine biosynthetic pathway from glutamate to ornithine synthesis step. Then putrescine is produced from the synthesized ornithine by ornithine decarboxylase (ODC). Therefore, in order to prepare a strain capable of producing high amount of putrescine, a sufficient amount of ornithine has to be made first. When glutamate was added to the argF- and argR-deleted strain of wild-type *E. coli* W3110, ornithine production level was increased by 20%. Also in addition to the pathway from glutamate to ornithine, when the pathway from glutamate to proline synthesis was blocked by knocking out proB gene which encodes γ-glutamylkinase involved in the first step thereof, the ornithine production level was increased as well. This suggests that when the intracellular level of glutamate is increased, it has positive effects on ornithine production in the cell. In a study of high yield production of glutamate which is a precursor of ornithine, *Corynebacterium glutamicum* has been studied for a long time. In this regard, it has been reported that the glutamate exporting activity of *Corynebacterium glutamicum* is enhanced when the cell lacks biotin or when the cell is treated with penicillin G or fatty acid ester surfactant. This result suggests that when the cell wall is damaged, glutamate can be exported better through cytoplasm.

NCgl1221 protein derived from *Corynebacterium glutamicum* wild-type strain (ATCC 13032) is known to promote the betain export and has a similar amino acid sequence as that of yggB which codes for a mechanosensitive channel protein (Korea Patent Publication No. 2010-0017581).

DISCLOSURE

Technical Problem

In effort of developing a strain capable of producing higher yield of putrescine, the present inventors have generated a strain producing high level of putrescine by blocking the biosynthetic pathway from ornithine to arginine, increasing the intracellular level of glutamate, enhancing the biosynthetic pathway from glutamate to ornithine, and by introducing an exogenous gene of ornithine decarboxylase which can synthesize putrescine from ornithine, thereby completing the present invention.

Technical Solution

One object of the present invention is to provide a microorganism given a ability to produce putrescine.

Another object of the present invention is to provide a method for producing putrescine by using the microorganism.

Advantageous Effect

A microorganism given the ability to produce putrescine of the present invention may be widely utilized for more effective putrescine production.

BRIEF DESCRIPTION OF THE DRAWINGS

FIG. 1 shows the biosynthetic pathway of putrescine and relevant genes in the transformed *Corynebacterium glutamicum* of the present invention.

FIG. 2 shows the biosynthetic pathway of arginine in the known *Corynebacterium glutamicum*.

FIG. 3 shows the vector pDZ to be inserted into the chromosome of *Corynebacterium* sp. strain.

BEST MODE

As one aspect to achieve the object of the present invention, the present invention provides a putrescine-producing microorganism, wherein the microorganism is modified to have diminished activity of an ornithine carbamoyltransferase and a protein involved in glutamate export, i.e., NCgl1221 compared to the endogenous activity thereof, and an activity of ornithine decarboxylase (ODC) is introduced into the microorganism.

As used herein, "ornithine carbamoyltransferase (OCT)" refers to a catalytic enzyme that mediates the reaction between carbamoyl phosphate and ornithine to synthesize citrulline and phosphoric acid. OCT is present in a liver of urea-excreting animals as well as plant and microorganism, and in microorganism it is involved in arginine synthesis. The OCT enzyme comprises catalytic domain and regulatory domain, and when ornithine binds to the regulatory domain the enzyme activity is inhibited.

*E. coli* K12 strain has two types of OCT (ArgF and ArgI), and intestinal microorganism including *E. coli* B and W strains have OCT protein similar to ArgI. OCTs encoded by argF and argI have different amino acid sequences from each other, but they are considered as isoenzyme having the same function (EMBO J. (1982) 1:853-857). *Corynebacterium* sp. strain only has OCT encoded by argF gene. OCT only acts in the synthetic pathway from ornithine to arginine, and thus if the OCT activity is diminished, the intracellular ornithine production level can be increased.

The present invention provides a *Corynebacterium* sp. strain wherein the synthetic pathway from ornithine to arginine is blocked to inhibit the conversion of a putrescine precursor, i.e. ornithine, to arginine. For this purpose, a transformant strain was prepared by deletion of the gene coding for the ornithine carbamoyl transferase.

The ornithine carbamoyltransferase may be a protein having an amino acid sequence of SEQ ID No. 28 or an amino acid sequence having 70% or more homology thereto, and preferably 80% or more, more preferably 90% or more homology thereto, but is not limited thereto.

As used herein, "homology" refers to the similarity in nucleotide sequences of gene coding for a protein or amino acid sequences. When homology is sufficiently high, products of the corresponding gene may be the same or have a similar activity.

As used herein, "protein involved in glutamate export" refers to a type of mechanosensitive channels which function to export the intracellularly produced glutamate to extracellular environment.

The present invention provides a *Corynebacterium* sp. strain given the ability to produce putrescine. For this purpose, a transformant strain that can maintain high cellular level of glutamate was prepared by deleting the gene coding for a protein involved in export of glutamate which is a substrate for the putrescine precursor, i.e. ornithine.

By increasing the intracellular level of glutamate, i.e., a precursor of ornithine, an ornithine biosynthetic pathway can be stimulated. In the present invention, glutamate exporting can be reduced or inhibited by diminishing the NCgl1221 activity.

The removed protein involved in glutamate export may be a protein having an amino acid sequence of SEQ ID No. 30 or an amino acid sequence having 70% or more homology thereto, and more preferably having 80% or more homology, even more preferably having 90% or more homology thereto, but is not limited thereto.

The activity of the ornithine carbamoyltransferase and the protein involved in glutamate export can be diminished by a method selected from the group consisting of (1) a partial or full deletion of a gene coding for the protein, (2) modification of an expression regulatory sequence for suppressing the gene expression, (3) modification of the nucleotide sequence on chromosome for diminishing the protein activity, and 4) a combination thereof, but is not limited thereto.

A partial or full deletion of a polynucleotide coding for the protein can be done by introducing a vector for chromosomal insertion into a microorganism, thereby substituting the polynucleotide coding for an endogenous target protein on chromosome with a partially removed polynucleotide or a marker gene. The length "partial" may vary depending on the type of polynucleotide, but specifically it refers to a length of 1 to 300 nucleotides, preferably 1 to 100 nucleotides, and more preferably 1 to 50 nucleotides.

Also, modification of an expression regulatory sequence for reducing expression of the polynucleotide can be done by inducing a modification on the expression regulatory sequence through deletion, insertion, non-conservative or conservative substitution of nucleotide sequence, or a combination thereof in order to diminish the activity of expression regulatory sequence, or by replacing the expression regulatory sequence with a nucleotide sequence having weaker activity. The expression regulatory sequence includes a promoter, an operator sequence, a sequence coding for ribosome-binding site, and a sequence regulating the termination of transcription and translation.

Furthermore, modification of a polynucleotide sequence on chromosome, which codes for the enzyme of the present invention can be done by inducing a mutation on the sequence through deletion, insertion, non-conservative or conservative substitution of polynucleotide sequence, or a combination thereof in order to diminish the enzymatic activity, or by replacing the sequence with a polynucleotide sequence which is modified to have weaker activity.

A transformant microorganism in which a precursor of putrescine, ornithine, is accumulated in the cell is prepared by different method from former methods for generating ornithine-producing strain (Korea Patent Publication No. 2010-0060909), that is, a method for increasing the ornithine production by eliminating or diminishing the function of ArgR which is a transcription inhibitor of arginine biosynthetic pathway, and additionally by deleting ornithine carbamoyltransferase gene and introducing unregulated N-acetylglutamate synthase.

As used herein, “endogenous activity” refers to the activity of enzyme that a microorganism possesses in its native state. In the present invention, endogenous activity refers to the activity of ornithine carbamoyl transferase and a protein involved in glutamate export, i.e., NCgl1221 that a microorganism naturally possesses. Also, as used herein, “modified to have a weaker activity than an endogenous activity” refers to the state where an ornithine carbamoyl transferase and a protein involved in glutamate export, i.e., NCgl1221 do not function properly due to gene deletion or mutation and thus the activity of ornithine carbamoyl transferase and a protein involved in glutamate export, i.e., NCgl1221 that a microorganism naturally possesses is weakened.

As used herein, “ornithine decarboxylase (ODC)” refers to an enzyme that produces putrescine using ornithine. The ODC requires pyridoxal 5'-phosphate (PLP) as a coenzyme. ODC is present in most of gram-negative bacteria, but it may be present in some of intestinal bacteria such as lactobacillus among gram-positive bacteria. *E. coli* possesses two types of genes coding for ODC. One of them is speC which is constitutively expressed at a constant concentration, and the other gene is speF whose expression is induced only under certain conditions (level of ornithine higher than a certain concentration and low pH). Depending on the species, some species have two types of ODC enzymes like in *E. coli*, or have only one type of ODC. To be specific, species including *Escherichia* sp., *Shigella* sp., *Citrobacter* sp., *Salmonella* sp., and *Enterobacter* sp. have two types of ODC (i.e., speC and speF), while species including *Yersinia* sp., *Klebsiella* sp., and *Erwinia* sp. have only one type of ODC (speC). In lactobacillus, ODC is expressed from one type of gene (speF), which is induced by low pH or high concentration of ornithine and histidine.

The ODC may be a protein coded by the amino acid sequence of SEQ ID No. 41 or the amino acid sequence having 70% or morehomology, more preferably 80% or more homology, even more preferably 90% or more homology, but is not limited thereto. As described above, the activity of ornithine decarboxylase (ODC) can be introduced by using various methods known in the art, for example, an insertion of a polynucleotide comprising ODC-coding nucleotide sequence into the chromosome, insertion of the polynucleotide into a vector system to be introduced to a microorganism, insertion of a promoter with improved activity on upstream of ODC-coding nucleotide sequence or insertion of an ODC-coding gene with a modified promoter, and insertion of a variant of ODC-coding nucleotide sequence. More preferably, when inserting the ODC-coding nucleotide sequence, a CJ7 promoter of SEQ ID No. 42 may be used as a promoter to regulate the expression of ODC.

In the example of the present invention, a microorganism of *Corynebacterium* sp. strain given the ability to produce putrescine is provided. To prepare a transformant capable of producing putrescine, the microorganism was inserted with the nucleotide sequence coding for ornithine decarboxylase in the chromosome which can synthesize putrescine from ornithine.

Putrescine produced by a microorganism may be degraded, in *E. coli* by an intracellular degradation pathway, into spermidine, acetyl putrescine, and gamma-aminobutyric acid (GABA). It is known that ODC is present in most of gram-negative strains, but not in *Corynebacterium* species. Therefore, when *Corynebacterium* sp. strains are used to generate a putrescine-producing strain, introduction of exogenous ODC is required.

As used herein, “a microorganism given the ability to produce putrescine” or “putrescine-producing microorganism” refers to a microorganism generated by giving the putrescine-producing ability to a mother strain which did not have the ability to produce putrescine intrinsically. The microorganism given the ability to produce putrescine or the putrescine-producing microorganism may be, but is not limited to, the microorganism wherein the activities of acetylglutamate synthase which converts glutamate to N-acetylglutamate, ornithine acetyltransferase (ArgJ) that converts acetyl ornithine to ornithine, acetylglutamate kinase (ArgB) that converts acetyl glutamate to N-acetylglutamyl phosphate, N-acetyl-gamma-glutamyl-phosphate reductase (ArgC) that converts acetyl glutamyl phosphate to N-acetyl glutamate semialdehyde, and acetylornithine aminotransferase (ArgD) that converts acetyl glutamate semialdehyde to N-acetylornithine, are enhanced compared to an intrinsic activity thereof, in order to enhance the biosynthetic pathway from glutamate to ornithine synthesis, thereby enhancing the productivity of ornithine which is used as a starting material for putrescine synthesis, and the microorganism that is transformed to introduce the gene coding for ornithine decarboxylase (speC), thereby acquiring the ability to produce putrescine from ornithine.

Here, the N-acetyl-gamma-glutamyl-phosphate reductase (ArgC), acetylglutamate synthase or ornithine acetyltransferase (ArgJ), acetylglutamate kinase (ArgB), and acetylornithine aminotransferase (ArgD) may preferably have, but is not limited to, an amino acid sequence of SEQ ID Nos. 33, 35, 37, and 39 respectively, or an amino acid sequence having 70% or more homology, more preferably 80% or more homology, and even more preferably 90% or more homology thereto. The activity of ArgC, ArgJ, ArgB, and ArgD can be enhanced by a method selected from the group consisting of 1) increase of the copy number of a polynucleotide coding for the protein, 2) modification of an expression regulatory sequence for increasing the polynucleotide expression, 3) modification of the polynucleotide sequence on a chromosome for enhancing an activity of the enzyme, and 4) a combination thereof.

To be specific, various methods can be used to increase the enzymatic activity in a microorganism in general. For example, the expression level of a polynucleotide can be increased by increasing the copy number of the polynucleotide through transformation involving plasmid insertion, homologous recombination, conjugation, and translocation; modifying an expression regulatory sequence of the polynucleotide; amplifying a gene coding for a regulatory factor which stimulates the polynucleotide expression; or by deleting or inhibiting a gene coding for a regulatory factor which suppresses the polynucleotide expression. To be more specific, the expression level of a polynucleotide can be increased by operably linking a gene fragment comprising the polynucleotide to a multicopy vector which can be replicated in *Corynebacterium* sp. strains, by introducing single or multiple copies of the polynucleotide to the chromosome, or replacing an expression regulatory sequence comprising the promoter of polynucleotide by the sequence having an improved activity.

For instance, the argCJBD gene group may be transformed into a microorganism by using pHC139T vector to prepare a microorganism with a significantly improved ability to produce ornithine compared to a wild-type strain. Alternatively, a microorganism in which ornithine biosynthetic pathway is enhanced may be prepared by improving a promoter region regulating the expression of argCJBD gene in the chromosome of microorganism to enhance the same or by replacing a promoter region by a promoter with more improved activity. In particular, a method for improving promoter region may involve, for replacing a promoter within the chromosome, preparing a gene fragment comprising nucleotide sequences of both terminal sites adjacent to the target site on the chromosome and a promoter sequence to be inserted in the same form as in the original chromosome and following the same gene deletion method using a pDZ vector published by Korea Patent Publication No. 2009-0082702, but is not limited thereto. Here, the improved promoter may preferably be, but is not limited to, the pcj7 (or P(CJ7)) promoter having a nucleotide sequence of SEQ ID No. 42 (Korea Patent Registration No. 0620092). The pDZ vector may preferably be, but is not limited to, a vector represented by a cleavage map of FIG. 3.

As used herein, "vector" refers to a DNA construct comprising a nucleotide sequence of gene which is operably linked to an appropriate expression regulatory sequence to express a target gene in a suitable host cell. The expression regulatory sequence comprises a promoter that can initiate transcription, an optional operator sequence for regulating the transcription, a sequence coding for a suitable mRNA ribosome binding site, and a sequence regulating the termination of transcription and translation. Examples of conventional vectors include a natural or recombinant plasmid, cosmid, virus and bacteriophage. For instance, pWE15, M13, λEMBL3, λEMBL4, λFIXII, λDASHII, λZAPII, λgt10, λgt11, Charon4A, and Charon21A can be used as a phage vector or cosmid vector. As a plasmid vector, pDZ vector, pBR type, pUC type, pBluescriptII type, pGEM type, pTZ type, pCL type and pET type may be used. A usable vector is not particularly limited, and any known expression vector, preferably pDZ vector, can be used.

Meanwhile, the microorganism of the present invention may be, but is not limited to, a transformant of the microorganism belonging to *Escherichia* sp., *Shigella* sp., *Citrobacter* sp., *Salmonella* sp., *Enterobacter* sp. *Yersinia* sp., *Klebsiella* sp., *Erwinia* sp., *Corynebacterium* sp., *Brevibacterium* sp., *Lactobacillus* sp., *Selenomanas* sp., or *Vibrio* sp. which does not possess putrescine metabolic pathway, while having the activity of ornithine carbamoyl transferase and a protein involved in glutamate export, i.e., NCgl1221.

Preferably the microorganism of the present invention may be a transformant in which ornithine is accumulated by reducing or inactivating the ornithine carbamoyl transferase activity, the intracellular level of glutamate is increased by reducing or inactivating the activity of a protein involved in glutamate export, ornithine is overproduced by increasing the expression level of argCJBD gene group which is involved in arginine biosynthesis, and exogenous gene coding for ornithine decarboxylase (ODC) that converts ornithine to putrescine is introduced, thereby making the cell capable of producing putrescine.

Preferably, the putrescine-producing microorganism of the present invention may be *Corynebacterium* sp. strain, and more preferably *Corynebacterium glutamicum*. To be more specific, a wild-type strain *Corynebacterium glutamicum* ATCC 13032 or a glutamate-overproducing strain KCCM-10785P (Korea Patent Publication No. 2008-0034334) may be used, but is not limited thereto. The KCCM-10785P strain is a glutamate-overproducing strain generated by deleting cg2624 (NCBI LOCUS ID YP_226636) and cg2115 (NCBI LOCUS ID YP_226173) genes in a glutamate-producing strain (KFCC-11074) which was generated by using mutagen such as N-methyl-N'-nitro-N-nitrosoguanidine (NTG).

Although glutamate overproduction by deletion of cg2624 and cg2115 have not been identified prior to the above publication, cg2624 is identified as pcaR, which is an IclR family regulatory protein, and cg2115 is identified as sugR, which is a transcriptional regulator of sugar metabolism.

As shown in the ornithine synthetic pathway of FIG. 2, in order to increase the production level of ornithine, it is required to increase the amount of a starting material, glutamate, block the pathway where the synthesized ornithine is converted into arginine, and increase the amount of enzyme involved in ornithine biosynthesis or enhance the activity thereof. Likewise, a transformed microorganism given the ability to produce putrescine can be prepared by increasing ornithine productivity, introducing a gene coding for ornithine decarboxylase (ODC) which can synthesize putrescine from ornithine to a microorganism lacking putrescine metabolic pathway, thereby inducing overproduction of ornithine.

According to the examples of the present invention, the following strains are prepared: argF-deleted *Corynebacterium glutamicum* strain (ATCC 13032 ΔargF and KCCM-10785P ΔargF) (Example 1), argF- and NCgl1221-deleted *Corynebacterium glutamicum* strain (ATCC 13032 ΔargF ΔNCgl1221 and KCCM-10785P ΔargF ΔNCgl1221) (Example 2), argF- and NCgl1221-deleted and argCJBD-inserted *Corynebacterium glutamicum* strain (ATCC 13032 ΔargF ΔNCgl1221/pHC139T-argCJBD(Cgl) and KCCM-10785P ΔargF ΔNCgl1221/pHC139T-argCJBD(Cgl)) (Example 3-1), argF- and NCgl1221-deleted *Corynebacterium glutamicum* strain with substitution of the promoter of argCJBD gene group in a chromosome (ATCC 13032 ΔargF ΔNCgl1221 P(CJ7)-argCJBD and KCCM-10785P ΔargF ΔNCgl1221 P(CJ7)-argCJBD) (Example 3-2), argF- and NCgl1221-deleted *Corynebacterium glutamicum* strain inserted with ODC-coding speC gene in the chromosome (ATCC 13032 ΔargF ΔNCgl1221 bioAD::P(CJ7)-speC(Ec) and KCCM-10785P ΔargF ΔNCgl1221 bioAD::P(CJ7)- speC(Ec)), argF- and NCgl1221-deleted *Corynebacterium glutamicum* strain inserted with ODC-coding speC gene and argCJBD gene group in the chromosome (ATCC 13032 ΔargF ΔNCgl1221 bioAD::P(CJ7)-speC(Ec)/pHC139T-argCJBD(Cgl) and KCCM-10785P ΔargF ΔNCgl1221 bioAD::P(CJ7)-speC(Ec)/pHC139T-argCJBD(Cgl)) and argF- and NCgl1221-deleted *Corynebacterium glutamicum* with substitution of the promoter of argCJBD gene group and insertion of speC gene in the chromosome (ATCC 13032 ΔargF ΔNCgl1221 P(CJ7)-argCJBD bioAD::P(CJ7)-speC(Ec) and KCCM-10785P ΔargF ΔNCgl1221 P(CJ7)-argCJBD bioAD::P(CJ7)-speC(Ec)). When putrescine productivity of these strains was compared, it was found that the argF- and NCgl1221-deleted *Corynebacterium glutamicum* strain with substitution of the promoter of argCJBD gene group and insertion of speC gene in the chromosome (ATCC 13032 ΔargF ΔNCgl1221 P(CJ7)-argCJBD bioAD::P(CJ7)-speC(Ec) and KCCM-10785P ΔargF ΔNCgl1221 P(CJ7)-argCJBD bioAD::P(CJ7)-speC(Ec)) showed excellent putrescine productivity (Tables 7 and 8).

As a result, the present inventors have named the putrescine-producing strain with the highest productivity as "CC01-0064 (ATCC 13032 ΔargF ΔNCgl1221 P(CJ7)-argCJBD bioAD::P(CJ7)-speC(Ec))", and deposited a sample of the strain under Budapest treaty to Korean Culture Center of Microorganisms (KCCM) located in Hongje 1-dong, Seodaemun-gu, Seoul, Korea in Nov. 24, 2010 with Accession No. KCCM11138P.

As another aspect to achieve the object of the present invention, the present invention provides a method for producing putrescine, comprising the step of (i) obtaining a cell culture by culturing a putrescine-producing microorganism; and (ii) recovering putrescine from the cultured microorganism or cell culture.

In the method of producing putrescine, culturing the microorganism may preferably be done by batch culture, continuous culture, and fed-batch culture known in the art, but is not limited thereto. Furthermore, as for the culturing condition, an optimal pH of 5 to 9, preferably pH 6 to 8, and most preferably pH 6.8 can be maintained by using a basic chemical (for example: sodium hydroxide, potassium hydroxide or ammonia) or acidic chemical (for example: phosphoric acid or sulfuric acid). Also, an aerobic condition can be maintained by adding oxygen or oxygen-containing gas mixture to a cell culture. The culturing temperature may be maintained at 20° C. to 45° C., and preferably at 25° C. to 40° C. In addition, it is preferable to culture for about 10 to 160 hours. The putrescine produced by the above culturing may be excreted to a culture medium or remain inside the cell.

Furthermore, the medium for culturing may comprise sugar and carbohydrate (for example: glucose, sucrose, lactose, fructose, maltose, molasse, starch and cellulose), oil and fat (for example: soybean oil, sunflower seed oil, peanut oil and coconut oil), fatty acid (for example: palmitic acid, stearic acid and linoleic acid), alcohol (for example: glycerol and ethanol), and organic acid (for example: acetic acid) individually or in combination as a carbon source; nitrogen-containing organic compound (for example: peptone, yeast extract, meat juice, malt extract, corn solution, soybean meal powder and urea), or inorganic compound (for example: ammonium sulfate, ammonium chloride, ammonium phosphate, ammonium carbonate, and ammonium nitrate) individually or in combination as a nitrogen source; potassium dihydrogen phosphate, dipotassium phosphate, or sodium-containing salt corresponding thereto individually or in combination as a phosphorus source; other essential growth-stimulating substances including metal salts (for example: magnesium sulfate or iron sulfate), amino acids, and vitamins.

Mode for Invention

Hereinafter, the present invention will be described in more detail with reference to Examples. However, these Examples are for illustrative purposes only, and the invention is not intended to be limited by these Examples.

Example 1: Preparation of argF-Deleted *Corynebacterium glutamicum* Strain

In this example, an argF-deleted strain was prepared from a wild-type *Corynebacterium glutamicum* strain ATCC 13032 and a glutamate-overproducing strain KCCM-10785P which was generated by deleting cg2624 and cg2115 genes in a glutamate-producing strain KFCC-11074 generated by using mutagen such as NTG (Korea Patent Publication No. 2008-0034334) in order to block a synthetic pathway of arginine from ornithine. The arginine biosynthetic genes of *Corynebacterium glutamicum* ATCC 13032 are organized in an operon having a form of argCJBDFRGH, and a deletion target argF gene (SEQ ID No. 27) is present adjacent to the genes coding for enzymes involved in ornithine synthetic pathway on the chromosome. Thus, a plasmid for deleting argF gene was prepared based on the nucleotide sequence of argD and argR which are located adjacent to the deletion target argF gene.

To be specific, based on the nucleotide sequence of argD and argR of the ATCC 13032 strain, a homologous recombination fragment adjacent to the N-terminal sequence of argF and a homologous recombination fragment adjacent to the C-terminal sequence of argF were constructed. For this, the fragment adjacent to the N-terminal sequence of argF was obtained by PCR using the genomic DNA from ATCC 13032 strain as a template, and primers (SEQ ID Nos. 1 and 2) (28 cycle of denaturation for 30 seconds at 94° C., annealing for 30 seconds at 55° C., and extension for 30 seconds at 72° C.). Likewise, the fragment adjacent to the C-terminal sequence of argF was obtained by PCR using the genomic DNA from ATCC 13032 strain as a template, and primers (SEQ ID Nos. 3 and 4) under same PCR condition (Table 1).

TABLE 1

Primers for preparing argF-deleted strain (ΔargF)

| Name | SEQ ID No. | Sequence(5'-3') |
|---|---|---|
| argF-del-F1_BamHI | 1 | CGGGATCCTGGCCGTACCGGCGATTTCT (SEQ ID NO: 1) |
| argF-del-R1_SalI | 2 | CGCGTCGACAAGTTTGAGTCCTTTATGCG (SEQ ID NO: 2) |

TABLE 1 -continued

| Primers for preparing argF-deleted strain (ΔargF) | | |
|---|---|---|
| Name | SEQ ID No. | Sequence(5'-3') |
| argF-del-F2_SalI | 3 | CGCGTCGACGACATGTCCCTTGGCTCAAC (SEQ ID NO: 3) |
| argF-del-R2_XbaI | 4 | TGCTCTAGAAGTAATTCACCTAGTTCTTTACC (SEQ ID NO: 4) |

The above-prepared homologous recombination fragment adjacent to the N-terminal sequence of argF was restriction digested with BamHI and SalI, and the homologous recombination fragment adjacent to the C-terminal sequence of argF was restriction digested with SalI and XbaI. Then each of the cleaved fragments were inserted into the pDZ vector which was also restriction digested with BamHI and XbaI, thereby producing a plasmid pDZ-argF(K/O).

The above-prepared plasmid pDZ-argF(K/O) was transformed into the ATCC 13032 strain and KCCM-10785P strain. Then, the transformed strains were plated and cultured on BHIS plate (Braine heart infusion 37 g/l, sorbitol 91 g/l, agar 2%) which contains kanamycin (25 μg/ml) and X-gal(5-bromo-4-chloro-3-indolin-β-D-galactoside), while letting the colonies to grow on the plate. Among the colonies formed on the plate, colonies with blue colour was collected to select for the strain inserted with the plasmid pDZ-argF (K/O).

The above-selected strains were cultured with shaking in CM medium (glucose 10 g/l, polypeptone 10 g/l, yeast extract 5 g/l, beef extract 5 g/l, NaCl 2.5 g/l, urea 2 g/l, pH 6.8) at 30° C. for 8 hours. Subsequently, each cell culture was serially diluted from $10^{-4}$ to $10^{-10}$. Then the diluted samples were plated and cultured on an X-gal-containing solid medium, letting the colonies to grow. Among the colonies formed on the plate, only the white colonies which appear at relatively low frequency were collected to select for the argF-deleted strains.

Successful insertion of the plasmid pDZargF(K/O) into the above-selected strains was confirmed by performing PCR using the chromosomal DNA from the above-selected strain as a template, and primers of SEQ ID Nos. 1 and 4. Through this PCR confirmation, it was confirmed that the above-selected strain is the argF-deleted strain (i.e., ATCC 13032 ΔargF and KCCM-10785P ΔargF).

Example 2: Preparation of argF- and NCgl1221-Deleted *Corynebacterium glutamicum* Strain The NCgl1221 gene encoding a protein involved in glutamate export was further deleted in ATCC 13032 ΔargF strain and KCCM-10785P ΔargF strain obtained in Example 1 in order to increase the intracellular level of glutamate which is an ornithine precursor.

To be specific, based on the nucleotide sequence (SEQ ID No. 29) of NCgl1221 of the ATCC 13032 strain, a homologous recombination fragment adjacent to the N-terminal sequence of NCgl1221 and a homologous recombination fragment adjacent to the C-terminal sequence of NCgl1221 were constructed. For this, the fragment adjacent to the N-terminal adjacent sequence of NCgl1221 was generated by PCR using the genomic DNA from ATCC 13032 strain as a template and primers (SEQ ID Nos. 5 and 6), and the fragment adjacent to the C-terminal sequence of NCgl1221 was generated by PCR using the genomic DNA from ATCC 13032 strain as a template and primers (SEQ ID Nos. 7 and 8) under the same PCR condition as in Example 1 (Table 2).

TABLE 2

| Primers for preparing NCgl1221-deleted strain | | |
|---|---|---|
| Name | SEQ ID No. | Sequence(5'-3') |
| NCgl1221-del-F1_BamHI | 5 | CGGGATCCGTCCAAGCCAAGCCGATTTCAAC (SEQ ID NO: 5) |
| NCgl1221-del-R1_SalI | 6 | ACGCGTCGACCCACTCGGCGCTTGATAATAC (SEQ ID NO: 6) |
| NCgl1221-del-F2_SalI | 7 | ACGCGTCGACCTGGAACAAGAACTCTCCAGC (SEQ ID NO: 7) |
| NCgl1221-del-R2_XbaI | 8 | CTAGTCTAGA GGTTGGTGCTTCCACTGCTG (SEQ ID NO: 8) |

The above-prepared homologous recombination fragment adjacent to the N-terminal sequence of NCgl1221 was restriction digested with BamHI and SalI. Likewise, the homologous recombination fragment adjacent to the C-terminal sequence of NCgl1221 was restriction digested with SalI and XbaI. Then each of the cleaved fragments was inserted into the pDZ vector that was cleaved with BamHI and XbaI, thereby producing a plasmid pDZ-NCgl1221(K/O).

The above-prepared plasmid pDZ-NCgl1221(K/O) was transformed into ATCC 13032 ΔargF strain and KCCM-10785P ΔargF strain. Then, the transformed strains were plated and cultured on BHIS plate (Braine heart infusion 37 g/l, sorbitol 91 g/l, agar 2%) which contains kanamycin (25 μg/ml) and X-gal(5-bromo-4-chloro-3-indolin-β-D-galactoside), while letting the colonies to grow on the plate. Among the colonies formed on the plate, colonies with blue colour was collected to select for the strain inserted with the plasmid pDZ-NCgl1221(K/O).

The above-selected strains were cultured with shaking in CM medium at 30° C. for 8 hours. Subsequently, each cell culture was serially diluted from $10^{-4}$ to $10^{-10}$. Then the diluted samples were plated and cultured on an X-gal-containing solid medium, letting the colonies to grow. Among the colonies formed on the plate, only the white colonies which appear at relatively low frequency were collected to select for the NCgl1221-deleted strains.

Successful insertion of the plasmid pDZ-NCgl1221(K/O) into the above-selected strains was confirmed by performing PCR using the chromosomal DNA from the above-selected strain as a template, and primers of SEQ ID Nos. 5 and 8. The selected NCgl1221-deleted strains were named as ATCC 13032 ΔargF ΔNCgl1221 or KCCM-10785P ΔargF ΔNCgl1221 accordingly.

Example 3: Preparation of argCJBD Gene-Inserted *Corynebacterium glutamicum* Strain

Example 3-1: Cloning of argCJBD Gene and Preparation of Transformant

In this example, a vector inserted with argC, argJ, argB, and argD genes (SEQ ID Nos. 32, 34, 36, and 38 respectively) was prepared and a transformant was prepared by introducing the same, in order to enhance the ornithine synthetic pathway by increasing the copy number of argCJBD operon (SEQ ID No. 31, comprising the promoter region) which codes for the enzymes involved in a synthetic pathway of ornithine from glutamate.

First, PCR was performed to obtain argCJBD gene by using the chromosome of ATCC 13032 strain as a template and primers (SEQ ID Nos. 9 and 10) (30 cycles of denaturation for 40 seconds at 95° C., annealing for 40 seconds at 55° C., and extension for 150 seconds at 72° C.), thereby obtaining a gene fragment having a size of 4,900 bp.

TABLE 3

Primers to obtain argCJBD gene fragment of ATCC 13032

| Name | SEQ ID No. | Sequence(5'-3') |
|---|---|---|
| P_argC-5-KpnI | 9 | CGGGGTACCCTCCTCCAGCAGCTCTAGCTC (SEQ ID NO: 9) |
| argD-3_XbaI | 10 | TGCTCTAGAAAGTTTGAGTCCTTTATGCG (SEQ ID NO: 10) |

The above-prepared gene fragment was run through gel electrophoresis on 0.8% agarose gel, and a band of the target size was cut and DNA sample was isolated therefrom. The isolated DNA was restriction digested with KpnI and XbaI to obtain a fragment, then the cleaved fragment was cloned into a pHC139T-gfp vector (Korea Patent Publication No. 2008-0074286), thereby producing an expression vector pHC139T-argCJBD(Cgl).

Subsequently, the expression vector pHC139T-argCJBD (Cgl) prepared for increasing the production level of ornithine in the cell was introduced into ATCC 13032 ΔargF ΔNCgl1221 strain and KCCM-10785P ΔargF ΔNCgl1221 strain through electroporation. Then, a successful transformant was selected by plating the transformed cells on BHIS plate containing 25 μg/ml kanamycin. Finally, each of the selected transformants was named as ATCC 13032 ΔargF ΔNCgl1221/pHC139T-argCJBD(Cgl) and KCCM-10785P ΔargF ΔNCgl1221/pHC139T-argCJBD(Cgl) accordingly.

Example 3-2: Substitution of the Promoter of argCJBD Gene in the Chromosome

In this example, a promoter of argCJBD was substituted with CJ7 promoter which was newly developed by the present applicant in the chromosome, in order to increase the expression level by removing the regulation of the argCJBD gene which codes for the enzymes involved in a synthetic pathway of ornithine from glutamate.

First, a homologous recombination fragment comprising a CJ7 promoter and a nucleotide sequence of both terminal sites of the promoter was prepared.

To be specific, the nucleotide sequence of 5'-terminal site of CJ7 promoter was obtained by performing PCR using the genomic DNA from ATCC 13032 strain as a template and primers (SEQ ID Nos. 11 and 12) (28 cycles of denaturation for 30 seconds at 94° C., annealing for 30 seconds at 55° C., and extension for 30 seconds at 72° C.). Likewise, the nucleotide sequence of CJ7 promoter region was obtained by PCR using primers (SEQ ID Nos. 13 and 14) under same PCR condition, and the nucleotide sequence of 3'-terminal site of CJ7 promoter was obtained by PCR using primers (SEQ ID Nos. 15 and 16) under same PCR condition.

TABLE 4

Primers for substituting the promoter of argCJBD gene

| Name | SEQ ID No. | Sequence (5'-3') |
|---|---|---|
| argC-L-5-BamHI | 11 | CGGGATCCGCAACGCTTGCGGTGAGAGA (SEQ ID NO: 11) |
| argC-L-3-EcoRI | 12 | CCGGAATTCCTGGAAGTGGTCGAAGAAGA (SEQ ID NO: 12) |
| CJ7-5-EcoRI | 13 | CCGGAATTCGCCGGCATAGCCTACCGATG (SEQ ID NO: 13) |
| CJ7-3-XbaI | 14 | TGCTCTAGAGATATCAGTGTTTCCTTTCG (SEQ ID NO: 14) |
| argC-R-5-XbaI | 15 | TGCTCTAGAATGATAATGCATAACGTGTA (SEQ ID NO: 15) |
| argC-R-3-SalI | 16 | ACGCGTCGACGCTTTCCGGAGGTGTTGTAC (SEQ ID NO: 16) |

The above-prepared 5'-terminal site fragment of promoter (argC-L) was restriction digested with BamHI and EcoRI, the CJ7 promoter region fragment was restriction digested with EcoRI and XbaI, and the 3'-terminal site fragment of promoter (argC-R) was restriction digested with XbaI and SalI. Then each of the cleaved PCR products was cloned into the pDZ vector which was also restriction digested with BamHI and SalI, thereby producing an expression vector pDZ-CJ7(arg) in which the promoter of argCJBD was substituted with CJ7 promoter.

The above-prepared expression vector pDZ-CJ7(arg) was transformed into ATCC 13032 ΔargF ΔNCgl1221 strain and KCCM-10785P ΔargF ΔNCgl1221 strain through electroporation. Then, the transformants were cultured with shaking in CM medium (30° C., 8 hours), and the cell culture was serially diluted from $10^{-4}$ to $10^{-10}$. Then, the diluted samples were placed and cultured on BHIS plate containing 25 μg/ml kanamycin and X-gal, letting the colonies to grow.

The white colonies which appear at low frequency were isolated from most of the blue colonies, thereby selecting only the strain where the arg promoter was successfully substituted with CJ7 promoter through double crossover. Successful substitution of argCJBD promoter in chromosome by the introduced expression vector pDZ-CJ7(arg) was confirmed by performing PCR using the genomic DNA from the above-selected strains as a template and primers (SEQ ID Nos. 13 and 16) (28 cycles of denaturation for 30 seconds at 94° C., annealing for 30 seconds at 55° C., and extension for 60 seconds at 72° C.). Finally, the confirmed strains were named as ATCC 13032 ΔargF ΔNCgl1221 P(CJ7)-argCJBD and KCCM-10785P ΔargF ΔNCgl1221 P(CJ7)-argCJBD accordingly.

Example 4: *Corynebacterium glutamicum* Strain Introduced with speC Gene

A speC gene coding for ODC of *E. coli* which synthesizes putrescine from ornithine was introduced within the inactivated biotin synthesis-related gene in the chromosome of *Corynebacterium glutamicum* strain.

Example 4-1: Preparation of Expression Vector Comprising a Gene Fragment of ODC In order to introduce the speC gene derived from *E. coli* (SEQ ID No. 40) into *Corynebacterium glutamicum* strain, speC gene was cloned into the vector along with a CJ7 promoter having SEQ ID No. 42 such that speC is expressed from the CJ7 promoter.

First, a nucleotide sequence of CJ7 promoter region was obtained by performing PCR using p117-CJ7-gfp (Korea Patent Registration No. 10620092) as a template and primers (SEQ ID Nos. 17 and 18) (30 cycles of denaturation for 40 seconds at 94° C., annealing for 40 seconds at 55° C., and extension for 60 seconds at 72° C.), and a nucleotide sequence of peC-coding region was obtained by performing PCR using the chromosome of wild-type *E. coli* strain W3110 as a template and primers (SEQ ID Nos. 19 and 20) under the same PCR condition.

TABLE 5

| Primers to obtain the P(CJ7)-speC gene fragment | | |
|---|---|---|
| Name | SEQ ID No. | Sequence (5'-3') |
| CJ7-5-KpnI | 17 | CGGGGTACCGCCGGCATAGCCTACCGATG (SEQ ID NO: 17) |
| CJ7-3 | 18 | p-GATATCAGTGTTTCCTTTCG (SEQ ID NO: 18) |
| speC(Ec)-5 | 19 | p-ATCATGAAATCAATGAATATTGCCG (SEQ ID NO: 19) |
| speC(Ec)-3_XbaI | 20 | TGCTCTAGATTACTTCAACACATAACCGTACAAC (SEQ ID NO: 20) |

The nucleotide sequences of CJ7 promoter region and speC-gene coding region were restriction digested with KpnI and XbaI, and cloned into the pHC139T-gfp vector which was also treated with KpnI and XbaI, thereby generating an expression vector pHC139T-P(CJ7)-speC(Ec) which comprises the genes for CJ7 promoter and ODC-coding region on downstream thereof.

Example 4-2: Preparation of Transformant

Since biotin synthesis-related genes are partially deleted in *Corynebacterium* sp. strain, in this example, speC gene derived from *E. coli* was introduced in between the biotin synthetic genes bioA and bioD.

To be specific, to use both terminal sites of P(CJ7)-speC (Ec) gene fragment comprised in the expression vector pHC139T-P(CJ7)-speC(Ec) prepared in Example 4-1 as homologous recombination sites in the *Corynebacterium* sp. strain chromosome, each of the terminal sites of P(CJ7)-speC(Ec) was cloned to have the nucleotide sequence of bioA and bioD. For this, bioA gene fragment was obtained by performing PCR using the genome of ATCC 13032 strain as a template and primers (SEQ ID Nos. 21 and 22) (28 cycles of denaturation for 40 seconds at 94° C., annealing for 30 seconds at 55° C., and extension for 60 seconds at 72° C.) Likewise, bioD gene fragment was obtained by performing PCR under the same PCR condition using the same template but different primers (SEQ ID Nos. 25 and 26). Then the P(CJ7)-speC(Ec) gene fragment was obtained by PCR using the expression vector pHC139T-P(CJ7)-speC(Ec) as a template and primers (SEQ ID Nos. 23 and 24) under the same PCR condition.

TABLE 6

| Primers for insertion of P(CJ7)-speC gene fragment within the chromosome (bioA, bioD) | | |
|---|---|---|
| Name | Seq ID No. | Sequence(5'-3') |
| bioA-5-BamHI | 21 | CGGGATCCTGCGCGAGCTTGATCACCGA (SEQ ID NO: 21) |
| bioA-3-ScaI | 22 | AAAAGTACTGCCTTGCCCACACACATGAT (SEQ ID NO: 22) |
| P(CJ7)-5-ScaI | 23 | AAAAGTACTGCCGGCATAGCCTACCGATG (SEQ ID NO: 23) |
| speC(Ec)-3-EcoRI | 24 | CCGGAATTCTTACTTCAACACATAACCGTACAAC (SEQ ID NO: 24) |
| bioD-5-EcoRI | 25 | CCGGAATTCGCTGTTTTGGCGGATGAGAG (SEQ ID NO: 25) |
| bioD-3-XbaI | 26 | TGCTCTAGACGCAAAAAGGCCATCCGTCA (SEQ ID NO: 26) |

The above-prepared bioA gene fragment was restriction digested with BamHI and ScaI, P(CJ7)-speC(Ec) gene fragment was restriction digested with ScaI and EcoRI, and bioD gene fragment was restriction digested with EcoRI and XbaI. Then these digested PCR products were cloned into the pDZ vector which was also treated with BamHI and XbaI, thereby generating the expression vector pDZ-bioAD-P(CJ7)-speC(Ec) for insertion of speC gene into the chromosome.

The above-prepared expression vector pDZ-bioAD-P(CJ7)-speC(Ec) was transformed into ATCC 13032 ΔargF ΔNCgl1221 strain, ATCC 13032 ΔargF ΔNCgl1221 P(CJ7)-argCJBD strain, KCCM-10785P ΔargF ΔNCgl1221 strain, and KCCM-10785P ΔargF ΔNCgl1221 P(CJ7)-argCJBD strain through electroporation, thereby generating the transformant of each strain.

Each of these transformants was cultured with shaking in CM medium (30° C., 8 hours), and the cell culture was serially diluted from $10^{-4}$ to $10^{-10}$. Then the diluted cell culture was plated and cultured on BHIS plate containing 25 μg/ml kanamycin and X-gal, letting the colonies form.

White colonies appear at relatively low frequency compared to majority of the colonies which have blue colour. By selecting the white colonies, only the strains where P(CJ7)-speC was inserted into the chromosome through double crossover could be selected. A successful insertion of P(CJ7)-speC gene in between bioA and bioD in the chromosome by the expression vector pDZ-bioAD-P(CJ7)-speC(Ec) was confirmed by performing PCR using the genomic DNA obtained from each of the selected strains as a template and primers (SEQ ID Nos. 21 and 26) (28 cycles of denaturation for 30 seconds at 94, annealing for 30 seconds at 55, and extension for 120 seconds at 72). Finally selected strains were named as ATCC 13032 ΔargF ΔNCgl1221 bioAD::P(CJ7)-speC(Ec), ATCC 13032 ΔargF ΔNCgl1221 P(CJ7)-argCJBD bioAD::P(CJ7)-speC(Ec), KCCM-10785P ΔargF ΔNCgl1221 bioAD::P(CJ7)-speC(Ec) or KCCM-10785P ΔargF ΔNCgl1221 P(CJ7)-argCJBD bioAD::P(CJ7)-speC(Ec) accordingly.

Furthermore, the pHC139T-argCJBD(Cgl) vector prepared in Example 3-1 was transformed into ATCC 13032 ΔargF ΔNCgl1221 bioAD::P(CJ7)-speC(Ec) strain and KCCM-10785P ΔargF ΔNCgl1221 bioAD::P(CJ7)-speC(Ec) strain. The prepared transformants were named as ATCC 13032 ΔargF ΔNCgl1221 bioAD::P(CJ7)-speC(Ec)/pHC139T-argCJBD(Cgl) and KCCM-10785P ΔargF ΔNCgl1221 bioAD::P(CJ7)-speC(Ec)/pHC139T-argCJBD(Cgl) accordingly.

Example 5: Effect of argF and NCgl1221 Deletion, Enhancement of argCJBD Expression Level, and Insertion of speC Gene in Improvement of Putrescine Productivity

Example 5-1: Analysis of Putrescine Productivity in ATCC 13032 *Corynebacterium glutamicum*

In order to confirm the effect of argF deletion, NCgl1221 deletion, enhancement of argCJBD expression level, and insertion of speC gene in putrescine productivity of ATCC 13032 *Corynebacterium glutamicum* strain, the putrescine productivities of the strains which were generated in Examples 2 to 4 were compared.

To be specific, each of the strains generated in Examples 2 to 4 (ATCC 13032 ΔargF ΔNCgl1221 (Test Group 1), ATCC 13032 ΔargF ΔNCgl1221/pHC139T-argCJBD(Cgl) (Test Group 2), ATCC 13032 ΔargF ΔNCgl1221 P(CJ7)-argCJBD (Test Group 3), ATCC 13032 ΔargF ΔNCgl1221 bioAD::P(CJ7)-speC(Ec) (Test Group 4), ATCC 13032 ΔargF ΔNCgl1221 bioAD::P(CJ7)-speC(Ec)/HC139T-argCJBD(Cgl) (Test Group 5) and ATCC 13032 ΔargF ΔNCgl1221 P(CJ7)-argCJBD bioAD::P(CJ7)-speC(Ec) (Test Group 6)) was spreaded on Corn Meal Agar (CMA) plate containing 11.8% (w/v) agar and cultured at 37 for 24 hours. Then, each of the cultured strains was inoculated into 25 ml titer medium comprising 1 mM arginine (2% (w/v) glucose, 1% (w/v) polypeptone, 0.5% (w/v) yeast extract, 0.5% (w/v) (NH4)2SO4, 0.15% (w/v) urea, 0.4% (w/v) KH2PO4, 0.8% (w/v) K2HPO4, 0.05% (w/v) MgSO4, 100 μg/l biotin and 1 mg/l thiamine) and further cultured with shaking at 30 and 200 rpm for 72 hours. Then the concentration of ornithine and putrescine produced therefrom was measured and compared (Table 7). Also, strain ATCC 13032 with no genomic modification was used as a control group.

TABLE 7

| Comparison of putrescine productivity in each of the mutant strains derived from ATCC 13032 strain | | |
|---|---|---|
| Test group | Ornithine(g/L) | Putrescine(g/L) |
| Control | 0.0 | 0.0 |
| 1 | 6.0 | 0.0 |
| 2 | 6.4 | 0.0 |
| 3 | 7.7 | 0.0 |
| 4 | 0.1 | 5.2 |
| 5 | 0.1 | 6.2 |
| 6 | 0.2 | 8.1 |

As shown in Table 7, when argF and NCgl1221 genes were deleted or when argF and NCgl1221 genes were deleted and argCJBD gene expression level was increased, only the production of ornithine was observed but putrescine was not produced in the cell. This might be caused by absence of speC gene which codes for ODC that synthesizes putrescine from ornithine in *Corynebacterium glutamicum* strain.

On the other hand, in three types of strains which were inserted with *E. coli*-derived speC gene as prepared in Example 4-2, ornithine was rarely present in the cell while production of putrescine was observed. This result suggests that through insertion of *E. coli*-derived speC gene which expresses ODC, putrescine could be synthesized from ornithine by ODC.

Also, when the production level of ornithine in the strains from Test Groups 1 to 3 was compared with the production level of putrescine in the strains from Test Groups 4 to 6 which were generated by inserting speC gene into the strains of Test Groups 1 to 3, it was evident that the production level of putrescine was comparable to the production level of ornithine. Furthermore, compared to when exogenous argCJBD gene was inserted, when the expression level of endogenous argCJBD gene was increased the production levels of ornithine and putrescine were improved.

Example 5-2: Examination of the Putrescine Productivity of Glutamate-Producing *Corynebacterium glutamicum* KCCM-10785P Strain In order to confirm the effect of argF deletion, NCgl1221 deletion, enhancement of argCJBD expression level, and insertion of speC gene in putrescine productivity of glutamate-overproducing *Corynebacterium glutamicum* strain KCCM-10785P, putrescine productivity of each of the strains generated in Examples 2 to 4 was compared.

To be specific, each of the strains generated in Examples 2 to 4 (KCCM-10785P ΔargF ΔNCgl1221 (Test Group 1), KCCM-10785P ΔargF ΔNCgl1221/pHC139T-argCJBD (Cgl) (Test Group 2), KCCM-10785P ΔargF ΔNCgl1221 P(CJ7)-argCJBD (Test Group 3), KCCM-10785P ΔargF ΔNCgl1221 bioAD::P(CJ7)-speC(Ec) (Test Group 4), KCCM-10785P ΔargF ΔNCgl1221 bioAD::P(CJ7)-speC (Ec)/HC139T-argCJBD(Cgl) (Test Group 5), and KCCM-10785P ΔargF ΔNCgl1221 P(CJ7)-argCJBD bioAD::P (CJ7)-speC(Ec) (Test Group 6)) was inoculated in the same condition as described in Example 5-1 and cultured with shaking at 30 and 200 rpm for 48 hours. Then the concentration of ornithine produced in each cell culture was measured and compared (Table 6). Also, KCCM-10785P strain with no genomic modification was used as a control group.

TABLE 8

| Comparison of putrescine productivity in each of the strains derived from KCCM-10785P strain | | | |
|---|---|---|---|
| Test group | Glutamate (g/L) | Ornithine (g/L) | Putrescine (g/L) |
| Control | 15.5 | 0.0 | 0.0 |
| 1 | 5.2 | 7.6 | 0.0 |
| 2 | 4.8 | 7.9 | 0.0 |
| 3 | 2.0 | 9.0 | 0.0 |
| 4 | 1.4 | 1.7 | 5.9 |
| 5 | 0.1 | 1.3 | 6.8 |
| 6 | 0.0 | 0.1 | 9.5 |

As shown in Table 8, when argF and NCgl1221 genes were deleted even in a glutamate-overproducing strain or when argF and NCgl1221 genes were deleted and the expression level of argCJBD gene was increased, only the production of ornithine was observed, but no putrescine was produced in the cell.

Meanwhile, production of putrescine was observed only in three types of strains which were introduced with *E. coli*-derived speC gene as prepared in Example 4-2. This result suggests that through introduction of *E. coli*-derived speC gene, the ODC enzyme expressed therefrom could synthesize putrescine from ornithine.

When the production levels of glutamate and ornithine in the strains of Test Groups 1 to 3 were compared, it was observed that as the production amount of glutamate was reduced, the production amount of ornithine was increased comparatively. Also, when the production level of ornithine in the strains of Test Groups 1 to 3 was compared with the production level of putrescine in the strains of Test Groups 4 to 6 which were generated by inserting speC gene into the strains of Test Groups 1 to 3, the production level of putrescine was comparable with the production level of ornithine. In addition, compared to when the exogenous argCJBD gene was inserted, when the expression level of intrinsic argCJBD gene was increased the production level of ornithine and putrescine was increased. In conclusion, it was confirmed that as the production level of glutamate in the cell is increased, the amount of ornithine is also increased, which in turn enhances the production level of putrescine in the end.

Overall, the present inventors have named the strain prepared in Example 4-2, which was proved to have an excellent ability to produce putrescine, as "CC01-0064 (ATCC 13032 ΔargF ΔNCgl1221 P(CJ7)-argCJBD bioAD:: P(CJ7)-speC(Ec))", and deposited this strain under Budapest treaty to Korean Culture Center of Microorganisms (KCCM) located in Hongje 1-dong, Seodaemun-gu, Seoul, Korea in Nov. 24, 2010 with Accession No. KCCM11138P.

Based on the above description, it should be understood by those skilled in the art that various alternatives to the embodiments of the invention described herein may be employed in practicing the invention without departing from the technical idea or essential features of the invention as defined in the following claims. In this regard, the above-described examples are for illustrative purposes only, and the invention is not intended to be limited by these examples. The scope of the present invention should be understood to include all of the modifications or modified form derived from the meaning and scope of the following claims or its equivalent concepts.

The invention claimed is:

1. A putrescine-producing recombinant microorganism, wherein the microorganism has been modified to reduce endogenous ornithine carbamoyltransferase activity and glutamate exporter activity compared to the corresponding unmodified microorganism, wherein the microorganism has been modified to express an ornithine decarboxylase (ODC), wherein the microorganism is a *Corynebacterium glutamicum,* wherein the glutamate exporter prior to the modification has an amino acid sequence comprising SEQ ID NO: 30, wherein the ornithine carbamoyltransferase prior to the modification has an amino acid sequence comprising SEQ ID NO: 28, and wherein the ornithine carbamoyltransferase activity and the glutamate exporter activity are reduced by a method selected from the group consisting of (i) a partial or full deletion of a gene coding for an endogenous ornithine carbamoyltransferase or an endogenous glutamate exporter, (ii) a modification of a regulatory region of a gene encoding an endogenous ornithine carbamoyltransferase or an endogenous glutamate exporter to reduce the gene expression, (iii) a modification of a gene coding for an endogenous ornithine carbamoyltransferase or coding for an endogenous glutamate exporter to reduce endogenous ornithine carbamoyltansferase activity or endogenous glutamate exporter activity, and (iv) any combination of (i), (ii), or (iii).

2. The putrescine-producing recombinant microorganism of claim 1, wherein the ornithine decarboxylase has an amino acid sequence comprising SEQ ID NO: 41.

3. The putrescine-producing recombinant microorganism of claim 1, wherein the microorganism is modified to express the ODC by a method selected from the group consisting of an insertion of a polynucleotide encoding the ODC into a chromosome, insertion of a polynucleotide encoding the ODC into a vector system to be introduced into the microorganism, insertion of a promoter with improved activity upstream of a polynucleotide encoding the ODC, and insertion of a gene encoding the ODC with a modified promoter.

4. The putrescine-producing recombinant microorganism of claim 1, wherein endogenous N-acetyl-gamma-glutamyl-phosphate reductase (ArgC) activity, endogenous N-acetyl-glutamate synthase or ornihthine acetyltransferase (ArgJ) activity, endogenous acetylglutamate kinase (ArgB) activity, and endogenous acetylornithine aminotransferase (ArgD) activity which are involved in biosynthesis of ornithine are further enhanced compared to the corresponding unmodified microorganism, wherein the ArgC activity, ArgJ activity, ArgB activity, and ArgD activity are enhanced by a method selected from the group consisting of (i) increasing of the copy number of a gene encoding ArgC, ArgJ, ArgB, or ArgD, (ii) modifying a regulatory region of a gene encoding the ArgC, ArgJ, ArgB, or ArgD to increase expression, (iii) a modification of an endogenous gene coding for ArgC, ArgJ, ArgB, or ArgD to enhance ArgC, ArgJ, ArgB, or ArgD activity, and (iv) any combination of (i), (ii), or (iii).

5. The putrescine-producing recombinant microorganism of claim 4, wherein the ArgC, ArgJ, ArgB, and ArgD have an amino acid sequence comprising SEQ ID NOs: 33, 35, 37, and 39 respectively.

6. The putrescine-producing recombinant microorganism of claim 1, wherein the *Corynebacterium glutamicum* is *Corynebacterium glutamicum* KCCM11138P.

7. A method for producing putrescine, comprising the step of (i) obtaining a cell culture by culturing the putrescine-producing recombinant microorganism according to claim 1; and (ii) recovering putrescine from the cultured microorganism or cell culture.

* * * * *

SEQUENCE LISTING

<160> NUMBER OF SEQ ID NOS: 42

<210> SEQ ID NO 1
<211> LENGTH: 28
<212> TYPE: DNA
<213> ORGANISM: Artificial Sequence
<220> FEATURE:
<223> OTHER INFORMATION: primer

<400> SEQUENCE: 1
cgggatcctg gccgtaccgg cgatttct 28

<210> SEQ ID NO 2
<211> LENGTH: 29
<212> TYPE: DNA
<213> ORGANISM: Artificial Sequence
<220> FEATURE:
<223> OTHER INFORMATION: primer

<400> SEQUENCE: 2
cgcgtcgaca agtttgagtc ctttatgcg 29

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
cgcgtcgacg acatgtccct tggctcaac 29

<210> SEQ ID NO 4
<211> LENGTH: 32
<212> TYPE: DNA
<213> ORGANISM: Artificial Sequence
<220> FEATURE:
<223> OTHER INFORMATION: primer

<400> SEQUENCE: 4
tgctctagaa gtaattcacc tagttcttta cc 32

<210> SEQ ID NO 5
<211> LENGTH: 31
<212> TYPE: DNA
<213> ORGANISM: Artificial Sequence
<220> FEATURE:
<223> OTHER INFORMATION: primer

<400> SEQUENCE: 5
acgcgtcgac ccactcggcg cttgataata c 31

<210> SEQ ID NO 6
<211> LENGTH: 31
<212> TYPE: DNA
<213> ORGANISM: Artificial Sequence
<220> FEATURE:
<223> OTHER INFORMATION: primer

<400> SEQUENCE: 6
acgcgtcgac ccactcggcg cttgataata c 31

<210> SEQ ID NO 7
<211> LENGTH: 31
<212> TYPE: DNA
<213> ORGANISM: Artificial Sequence
<220> FEATURE:
<223> OTHER INFORMATION: primer

<400> SEQUENCE: 7
acgcgtcgac ctggaacaag aactctccag c 31

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
ctagtctaga ggttggtgct tccactgctg 30

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
cggggtaccc tcctccagca gctctagctc 30

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
tgctctagaa agtttgagtc ctttatgcg 29

<210> SEQ ID NO 11
<211> LENGTH: 28
<212> TYPE: DNA
<213> ORGANISM: Artificial Sequence
<220> FEATURE:
<223> OTHER INFORMATION: primer

<400> SEQUENCE: 11
cgggatccgc aacgcttgcg gtgagaga 28

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
ccggaattcc tggaagtggt cgaagaaga 29

<210> SEQ ID NO 13
<211> LENGTH: 29
<212> TYPE: DNA
<213> ORGANISM: Artificial Sequence
<220> FEATURE:
<223> OTHER INFORMATION: primer

<400> SEQUENCE: 13
ccggaattcg ccggcatagc ctaccgatg 29

<210> SEQ ID NO 14
<211> LENGTH: 29
<212> TYPE: DNA
<213> ORGANISM: Artificial Sequence
<220> FEATURE:
<223> OTHER INFORMATION: primer

<400> SEQUENCE: 14
tgctctagag atatcagtgt ttcctttcg 29

<210> SEQ ID NO 15
<211> LENGTH: 29
<212> TYPE: DNA
<213> ORGANISM: Artificial Sequence
<220> FEATURE:
<223> OTHER INFORMATION: primer

<400> SEQUENCE: 15
tgctctagaa tgataatgca taacgtgta 29

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
acgcgtcgac gctttccgga ggtgttgtac 30

<210> SEQ ID NO 17
<211> LENGTH: 29
<212> TYPE: DNA
<213> ORGANISM: Artificial Sequence
<220> FEATURE:
<223> OTHER INFORMATION: primer

<400> SEQUENCE: 17
cggggtaccg ccggcatagc ctaccgatg 29

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
gatatcagtg tttcctttcg 20

<210> SEQ ID NO 19
<211> LENGTH: 25
<212> TYPE: DNA
<213> ORGANISM: Artificial Sequence
<220> FEATURE:
<223> OTHER INFORMATION: primer

<400> SEQUENCE: 19
atcatgaaat caatgaatat tgccg 25

<210> SEQ ID NO 20
<211> LENGTH: 34
<212> TYPE: DNA
<213> ORGANISM: Artificial Sequence
<220> FEATURE:
<223> OTHER INFORMATION: primer

<400> SEQUENCE: 20
tgctctagat tacttcaaca cataaccgta caac 34

<210> SEQ ID NO 21
<211> LENGTH: 28
<212> TYPE: DNA
<213> ORGANISM: Artificial Sequence
<220> FEATURE:
<223> OTHER INFORMATION: primer

<400> SEQUENCE: 21
cgggatcctg cgcgagcttg atcaccga 28

<210> SEQ ID NO 22
<211> LENGTH: 29
<212> TYPE: DNA
<213> ORGANISM: Artificial Sequence
<220> FEATURE:
<223> OTHER INFORMATION: primer

<400> SEQUENCE: 22
aaaagtactg ccttgcccac acacatgat 29

<210> SEQ ID NO 23
<211> LENGTH: 29
<212> TYPE: DNA
<213> ORGANISM: Artificial Sequence
<220> FEATURE:
<223> OTHER INFORMATION: primer

<400> SEQUENCE: 23
aaaagtactg ccggcatagc ctaccgatg 29

<210> SEQ ID NO 24
<211> LENGTH: 34
<212> TYPE: DNA
<213> ORGANISM: Artificial Sequence
<220> FEATURE:
<223> OTHER INFORMATION: primer

<400> SEQUENCE: 24
ccggaattct tacttcaaca cataaccgta caac 34

<210> SEQ ID NO 25
<211> LENGTH: 29
<212> TYPE: DNA
<213> ORGANISM: Artificial Sequence
<220> FEATURE:
<223> OTHER INFORMATION: primer

<400> SEQUENCE: 25
ccggaattcg ctgttttggc ggatgagag 29

<210> SEQ ID NO 26
<211> LENGTH: 29
<212> TYPE: DNA
<213> ORGANISM: Artificial Sequence
<220> FEATURE:
<223> OTHER INFORMATION: primer

<400> SEQUENCE: 26
tgctctagac gcaaaaaggc catccgtca 29

<210> SEQ ID NO 27

```
<211> LENGTH: 960
<212> TYPE: DNA
<213> ORGANISM: Corynebacterium glutamicum

<400> SEQUENCE: 27

atgacttcac aaccacaggt tcgccatttt ctggctgatg atgatctcac ccctgcagag      60

caggcagagg ttttgaccct agccgcaaag ctcaaggcag cgccgttttc ggagcgtcca     120

ctcgagggac caaagtccgt tgcagttctt tttgataaga cttcaactcg tactcgcttc     180

tccttcgacg cgggcatcgc tcatttgggt ggacacgcca tcgtcgtgga ttccggtagc     240

tcacagatgg gtaagggcga gtccctgcag gacaccgcag ctgtattgtc ccgctacgtg     300

gaagcaattg tgtggcgcac ctacgcacac agcaatttcc acgccatggc ggagacgtcc     360

actgtgccgc tggtgaactc cttgtccgat gatctgcacc catgccagat tctggctgat     420

ctgcagacta tcgtggaaaa cctcagccct gaagaaggcc cagcaggcct taagggtaag     480

aaggctgtgt acctgggcga tggcgacaac aacatggcca actcctacat gattggcttt     540

gccaccgcgg gcatggatat ttccatcatc gctcctgaag ggttccagcc tcgtgcggaa     600

ttcgtggagc gcgcggaaaa gcgtggccag gaaaccggcg cgaaggttgt tgtcaccgac     660

agcctcgacg aggttgccgg cgccgatgtt gtcatcaccg atacctgggt atccatgggt     720

atggaaaacg acggcatcga tcgcaccaca cctttcgttc cttaccaggt caacgatgag     780

gtcatggcga aagctaacga cggcgccatc ttcctgcact gccttcctgc ctaccgtggc     840

aaagaagtgg cagcctccgt gattgatgga ccagcgtcca aagttttcga tgaagcagaa     900

aaccgcctcc acgctcagaa agcactgctg gtgtggctgc tggccaacca gccgaggtaa     960


<210> SEQ ID NO 28
<211> LENGTH: 319
<212> TYPE: PRT
<213> ORGANISM: Corynebacterium glutamicum

<400> SEQUENCE: 28

Met Thr Ser Gln Pro Gln Val Arg His Phe Leu Ala Asp Asp Asp Leu
1               5                   10                  15

Thr Pro Ala Glu Gln Ala Glu Val Leu Thr Leu Ala Ala Lys Leu Lys
            20                  25                  30

Ala Ala Pro Phe Ser Glu Arg Pro Leu Glu Gly Pro Lys Ser Val Ala
        35                  40                  45

Val Leu Phe Asp Lys Thr Ser Thr Arg Thr Arg Phe Ser Phe Asp Ala
    50                  55                  60

Gly Ile Ala His Leu Gly Gly His Ala Ile Val Val Asp Ser Gly Ser
65                  70                  75                  80

Ser Gln Met Gly Lys Gly Glu Ser Leu Gln Asp Thr Ala Ala Val Leu
                85                  90                  95

Ser Arg Tyr Val Glu Ala Ile Val Trp Arg Thr Tyr Ala His Ser Asn
            100                 105                 110

Phe His Ala Met Ala Glu Thr Ser Thr Val Pro Leu Val Asn Ser Leu
        115                 120                 125

Ser Asp Asp Leu His Pro Cys Gln Ile Leu Ala Asp Leu Gln Thr Ile
    130                 135                 140

Val Glu Asn Leu Ser Pro Glu Glu Gly Pro Ala Gly Leu Lys Gly Lys
145                 150                 155                 160

Lys Ala Val Tyr Leu Gly Asp Gly Asp Asn Asn Met Ala Asn Ser Tyr
                165                 170                 175
```

```
Met Ile Gly Phe Ala Thr Ala Gly Met Asp Ile Ser Ile Ile Ala Pro
            180                 185                 190

Glu Gly Phe Gln Pro Arg Ala Glu Phe Val Glu Arg Ala Glu Lys Arg
        195                 200                 205

Gly Gln Glu Thr Gly Ala Lys Val Val Val Thr Asp Ser Leu Asp Glu
    210                 215                 220

Val Ala Gly Ala Asp Val Val Ile Thr Asp Thr Trp Val Ser Met Gly
225                 230                 235                 240

Met Glu Asn Asp Gly Ile Asp Arg Thr Thr Pro Phe Val Pro Tyr Gln
                245                 250                 255

Val Asn Asp Glu Val Met Ala Lys Ala Asn Asp Gly Ala Ile Phe Leu
            260                 265                 270

His Cys Leu Pro Ala Tyr Arg Gly Lys Glu Val Ala Ala Ser Val Ile
        275                 280                 285

Asp Gly Pro Ala Ser Lys Val Phe Asp Glu Ala Glu Asn Arg Leu His
    290                 295                 300

Ala Gln Lys Ala Leu Leu Val Trp Leu Leu Ala Asn Gln Pro Arg
305                 310                 315


<210> SEQ ID NO 29
<211> LENGTH: 1602
<212> TYPE: DNA
<213> ORGANISM: Corynebacterium glutamicum

<400> SEQUENCE: 29

atgattttag gcgtacccat tcaatatttg ctctattcat tgtggaattg gattgtcgat      60

accggttttg atgtagcaat tatcctggtc ttggcgtttt tgattccacg tatcggccga     120

ctggccatgc gtattatcaa gcgccgagtg gagtctgcag ccgatgcgga caccactaag     180

aaccagctcg cgttcgccgg cgttggcgtt tatatcgcgc aaattgtggc gtttttcatg     240

cttgccgtct ccgcgatgca ggcttttggt ttctctctcg cgggcgctgc gattccggca     300

accattgcgt cagctgccat tggccttggt gcgcagtcga ttgttgcgga cttcttggcc     360

ggatttttca tcctgacgga aaagcaattc ggcgtgggtg actgggtgcg ttttgagggc     420

aacggcatcg ttgtcgaagg caccgtcatt gagatcacca tgcgcgcgac caaaattcgc     480

acgattgcac aagagaccgt gatcatcccc aactccacgg cgaaagtgtg catcaacaat     540

tctaataact ggtcgcgtgc ggttgtcgtt attccgatcc ccatgttggg ttctgaaaac     600

atcacagatg tcatcgcgcg ctctgaagct gcgactcgtc gcgcacttgg ccaggagaaa     660

atcgcaccgg aaatcctcgg tgaactcgat gtgcacccag ccacggaagt cacgccgcca     720

acggtggtcg gcatgccgtg gatggtcacc atgcgtttcc tcgtgcaagt caccgccggc     780

aatcaatggc tggtcgaacg cgccatccgc acagaaatca tcagcgaatt ctgggaagaa     840

tacggcagcg caaccactac atcgggaacc ctcattgatt ccttacacgt tgagcatgaa     900

gagccaaaga cctcgcttat cgacgcctcc ccccaggctc ttaaggaacc gaagccggag     960

gctgcggcga cggttgcatc gctagctgca tcctctaacg acgatgcaga caatgcagac    1020

gcctcggtga tcaatgcagg caatccagag aaggaacttg attccgatgt gctggaacaa    1080

gaactctcca gcgaagaacc ggaagaaaca gcaaaaccag atcactctct ccgaggcttc    1140

ttccgcactg attactaccc aaatcggtgg cagaagatcc tgtcgtttgg cggacgtgtc    1200

cgcatgagca cgtccctgtt gttgggtgcg ctgctcttgc tgtcactatt taaggtcatg    1260

actgtggaac caagtgagaa ttggcaaaac tccagtggat ggctgtcacc aagcactgcc    1320
```

```
acctcaactg cggtgaccac ctccgaaact tccgcgccag taagcacgcc ttcgatgaca   1380

gtgcccacta cggtggagga gaccccaacg atggaatcta acgtcgaaac gcagcaggaa   1440

acctcaaccc ctgcaaccgc aacgccccag cgagccgaca ccatcgaacc gaccgaggaa   1500

gccacgtcgc aggaggaaac gactgcgtcg cagacgcagt ctccagcagt ggaagcacca   1560

accgcggtcc aagagacagt tgcgccgacg tccacccctt ag                     1602


<210> SEQ ID NO 30
<211> LENGTH: 533
<212> TYPE: PRT
<213> ORGANISM: Corynebacterium glutamicum

<400> SEQUENCE: 30

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Arg
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Ser Glu Phe Trp Glu Glu Tyr Gly Ser Ala Thr Thr Thr Ser
        275                 280                 285

Gly Thr Leu Ile Asp Ser Leu His Val Glu His Glu Glu Pro Lys Thr
    290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
```

-continued 325 330 335

Asp Asn Ala Asp Ala Ser Val Ile Asn Ala Gly Asn Pro Glu Lys Glu
340 345 350

Leu Asp Ser Asp Val Leu Glu Gln Glu Leu Ser Ser Glu Glu Pro Glu
355 360 365

Glu Thr Ala Lys Pro Asp His Ser Leu Arg Gly Phe Phe Arg Thr Asp
370 375 380

Tyr Tyr Pro Asn Arg Trp Gln Lys Ile Leu Ser Phe Gly Gly Arg Val
385 390 395 400

Arg Met Ser Thr Ser Leu Leu Leu Gly Ala Leu Leu Leu Leu Ser Leu
405 410 415

Phe Lys Val Met Thr Val Glu Pro Ser Glu Asn Trp Gln Asn Ser Ser
420 425 430

Gly Trp Leu Ser Pro Ser Thr Ala Thr Ser Thr Ala Val Thr Thr Ser
435 440 445

Glu Thr Ser Ala Pro Val Ser Thr Pro Ser Met Thr Val Pro Thr Thr
450 455 460

Val Glu Glu Thr Pro Thr Met Glu Ser Asn Val Glu Thr Gln Gln Glu
465 470 475 480

Thr Ser Thr Pro Ala Thr Ala Thr Pro Gln Arg Ala Asp Thr Ile Glu
485 490 495

Pro Thr Glu Glu Ala Thr Ser Gln Glu Glu Thr Thr Ala Ser Gln Thr
500 505 510

Gln Ser Pro Ala Val Glu Ala Pro Thr Ala Val Gln Glu Thr Val Ala
515 520 525

Pro Thr Ser Thr Pro
530

<210> SEQ ID NO 31
<211> LENGTH: 4733
<212> TYPE: DNA
<213> ORGANISM: Corynebacterium glutamicum

<400> SEQUENCE: 31
ggctacttcc gaggaatctt ccgcagttga agagccagca gtggaagctc ctgtggaaga 60
ggctccagtc gaggcacctg ttgagcaggc acctgtcgtg gagcaagctc cagttgagca 120
ggctccggca ccggttcagg aagcacctgc accagtcgag caggctccag ctccagttca 180
ggaagcacct gcagctgacg cgccacctgc acttccaggt ggtggcggcg gacacgctgg 240
ctactaaaaa ttcatgcttt tacccacttg cagttttagc tgtaggtggg tttttgcatg 300
tctaacccgt cttttatgca cacccccgca atgaatcaaa aatttatgca tgaataattt 360
gcatgatcat gcataacgtg tatggtgtaa ctatgacaat caaggttgca atcgcaggag 420
ccagtggata tgccggcgga gaaatccttc gtctcctttt aggccatcca gcttatgcat 480
ctggtgaact agaaatcgga gcactcaccg cggcatcaac cgcaggcagc acgctcggtg 540
aattgatgcc acacattccg cagttggcgg atcgtgttat tcaagacacc acagctgaaa 600
ctctagccgg tcatgatgtc gtatttctag gacttccaca cggattctct gcagaaattg 660
cacttcagct cggaccagat gtcacagtga ttgactgtgc agctgacttt cgtctgcaaa 720
atgctgcaga ttgggagaag ttctacggct cagagcacca gggaacatgg ccttatggca 780
ttccagaaat gccaggacac cgcgaggctc ttcgtggtgc taagcgtgta gcagtgccag 840
gatgtttccc aaccggtgca accttggctc ttcttcctgc ggttcaagcg ggacttatcg 900

-continued

```
agccagatgt ttccgtagtg tccatcaccg gcgtatcagg tgcaggtaag aaagcatctg    960
ttgcactact tggctcggaa accatgggtt cactcaaggc gtacaacacc tccggaaagc   1020
accgccacac cccggaaatt gcccagaacc tcggcgaagt cagcgacaag ccagtcaagg   1080
tgagcttcac cccagtgctt gcaccgttac ctcgcggaat tctcaccact gcaaccgcac   1140
ctttgaaaga aggcgttacc gcagaacagg ctcgcgcagt atatgaagag ttctatgcac   1200
aggaaacctt cgtgcatgtt cttccagaag gtgcacagcc acaaacccaa gcagttcttg   1260
gctccaacat gtgccacgtg caggtagaaa ttgatgagga agcaggcaaa gtccttgtta   1320
cctccgcaat cgataacctc accaagggaa ctgccggcgc cgctgttcag tgcatgaact   1380
taagcgttgg ttttgatgag gcagcaggcc tgccacaggt cggcgtcgca ccttaaatgg   1440
cagaaaaagg cattaccgcg ccgaaaggct tcgttgcttc tgcaacgacc gcgggtatta   1500
aagcttctgg caatcctgac atggcgttgg tggttaacca gggtccagag ttttccgcag   1560
cggccgtgtt tacacgtaac cgagttttcg cagcgcctgt gaaggtgagc cgagagaacg   1620
ttgctgatgg ccagatcagg gctgttttgt acaacgctgg taatgctaat gcgtgtaatg   1680
gtctgcaggg tgagaaggat gctcgtgagt ctgtttctca tctagctcaa aatttgggct   1740
tggaggattc cgatattggt gtgtgttcca ctggtcttat tggtgagttg cttccgatgg   1800
ataagctcaa tgcaggtatt gatcagctga ccgctgaggg cgctttgggt gacaatggtg   1860
cagctgctgc caaggcgatc atgaccactg acacggtgga taaggaaacc gtcgtgtttg   1920
ctgatggttg gactgtcggc ggaatgggca agggcgtggg catgatggcg ccgtctcttg   1980
ccaccatgct ggtctgcttg accactgatg catccgttac tcaggaaatg gctcagatcg   2040
cgctggctaa tgctacggcc gttacgtttg acaccctgga tattgatgga tcaacctcca   2100
ccaatgacac cgtgttcctg ctggcatctg gcgctagcgg aatcacccca actcaggatg   2160
aactcaacga tgcggtgtac gcagcttgtt ctgatatcgc agcgaagctt caggctgatg   2220
cagagggtgt gaccaagcgc gttgctgtga cagtggtggg aaccaccaac aacgagcagg   2280
cgattaatgc ggctcgcact gttgctcgtg acaatttgtt caagtgcgca atgtttggat   2340
ctgatccaaa ctggggtcgc gtgttggctg cagtcggcat ggctgatgct gatatggaac   2400
cagagaagat ttctgtgttc ttcaatggtc aagcagtatg ccttgattcc actggcgctc   2460
ctggtgctcg tgaggtggat ctttccggcg ctgacattga tgtccgaatt gatttgggca   2520
ccagtgggga aggccaggca acagttcgaa ccactgacct gagcttctcc tacgtggaga   2580
tcaactccgc gtacagctct taaatgaatg acttgatcaa agatttaggc tctgaggtgc   2640
gcgcaaatgt cctcgctgag gcgttgccat ggttgcagca cttccgcgac aagattgttg   2700
tcgtgaaata tggcggaaac gccatggtgg atgatgatct caaggctgct tttgctgccg   2760
acatggtctt cttgcgcacc gtgggcgcaa aaccagtggt ggtgcacggt ggtggacctc   2820
agatttctga gatgctaaac cgtgtgggtc tccagggcga gttcaagggt ggtttccgtg   2880
tgaccactcc tgaggtcatg gacattgtgc gcatggtgct ctttggtcag gtcggtcgcg   2940
atttagttgg tttgatcaac tctcatggcc cttacgctgt gggaacctcc ggtgaggatg   3000
ccggcctgtt taccgcgcag aagcgcatgg tcaacatcga tggcgtaccc actgatattg   3060
gtttggtcgg agacatcatt aatgtcgatg cctcttcctt gatggatatc atcgaggccg   3120
gtcgcattcc tgtggtctct acgattgctc caggcgaaga cggccagatt tacaacatta   3180
acgccgatac cgcagcaggt gctttggctg cagcgattgg tgcagaacgc ctgctggttc   3240
tcaccaatgt ggaaggtctg tacaccgatt ggcctgataa gagctcactg gtgtccaaga   3300
```

```
tcaaggccac cgagctggag gccattcttc cgggacttga ttccggcatg attccaaaga   3360
tggagtcttg cttgaacgcg gtgcgtgggg gagtaagcgc tgctcatgtc attgacggcc   3420
gcatcgcgca ctcggtgttg ctggagcttt tgaccatggg tggaattggc acgatggtgc   3480
tgccggatgt ttttgatcgg gagaattatc ctgaaggcac cgtttttaga aaagacgaca   3540
aggatgggga actgtaaatg agcacgctgg aaacttggcc acaggtcatt attaatacgt   3600
acggcacccc accagttgag ctggtgtccg gcaagggcgc aaccgtcact gatgaccagg   3660
gcaatgtcta catcgacttg ctcgcgggca tcgcagtcaa cgcgttgggc cacgcccacc   3720
cggcgatcat cgaggcggtc accaaccaga tcggccaact tggtcacgtc tcaaacttgt   3780
tcgcatccag gcccgtcgtc gaggtcgccg aggagctcat caagcgtttt tcgcttgacg   3840
acgccaccct cgccgcgcaa acccgggttt tcttctgcaa ctcgggcgcc gaagcaaacg   3900
aggctgcttt caagattgca cgcttgactg gtcgttcccg gattctggct gcagttcatg   3960
gtttccacgg ccgcaccatg ggttccctcg cgctgactgg ccagccagac aagcgtgaag   4020
cgttcctgcc aatgccaagc ggtgtggagt tctaccctta cggcgacacc gattacttgc   4080
gcaaaatggt agaaaccaac ccaacggatg tggctgctat cttcctcgag ccaatccagg   4140
gtgaaacggg cgttgttcca gcacctgaag gattcctcaa ggcagtgcgc gagctgtgcg   4200
atgagtacgg catcttgatg atcaccgatg aagtccagac tggcgttggc cgtaccggcg   4260
atttctttgc acatcagcac gatggcgttg ttcccgatgt ggtgaccatg gccaagggac   4320
ttggcggcgg tcttcccatc ggtgcttgtt tggccactgg ccgtgcagct gaattgatga   4380
ccccaggcaa gcacggcacc actttcggtg gcaacccagt tgcttgtgca gctgccaagg   4440
cagtgctgtc tgttgtcgat gacgctttct gcgcagaagt tgcccgcaag ggcgagctgt   4500
tcaaggaact tcttgccaag gttgacggcg ttgtagacgt ccgtggcagg ggcttgatgt   4560
tgggcgtggt gctggagcgc gacgtcgcaa agcaagctgt tcttgatggt tttaagcacg   4620
gcgttatttt gaatgcaccg gcggacaaca ttatccgttt gaccccgccg ctggtgatca   4680
ccgacgaaga aatcgcagac gcagtcaagg ctattgccga gacaatcgca taa          4733
```

<210> SEQ ID NO 32
<211> LENGTH: 1074
<212> TYPE: DNA
<213> ORGANISM: Corynebacterium glutamicum

<400> SEQUENCE: 32

```
atgatcatgc ataacgtgta tggtgtaact atgacaatca aggttgcaat cgcaggagcc     60
agtggatatg ccggcggaga aatccttcgt ctcctttttag gccatccagc ttatgcatct   120
ggtgaactag aaatcggagc actcaccgcg gcatcaaccg caggcagcac gctcggtgaa    180
ttgatgccac acattccgca gttggcggat cgtgttattc aagacaccac agctgaaact    240
ctagccggtc atgatgtcgt atttctagga cttccacacg gattctctgc agaaattgca    300
cttcagctcg gaccagatgt cacagtgatt gactgtgcag ctgactttcg tctgcaaaat    360
gctgcagatt gggagaagtt ctacggctca gagcaccagg gaacatggcc ttatggcatt    420
ccagaaatgc caggacaccg cgaggctctt cgtggtgcta agcgtgtagc agtgccagga    480
tgtttcccaa ccggtgcaac cttggctctt cttcctgcgg ttcaagcggg acttatcgag    540
ccagatgttt ccgtagtgtc catcaccggc gtatcaggtg caggtaagaa agcatctgtt    600
gcactacttg gctcggaaac catgggttca ctcaaggcgt acaacacctc cggaaagcac    660
```

```
cgccacaccc cggaaattgc ccagaacctc ggcgaagtca gcgacaagcc agtcaaggtg    720

agcttcaccc cagtgcttgc accgttacct cgcggaattc tcaccactgc aaccgcacct    780

ttgaaagaag gcgttaccgc agaacaggct cgcgcagtat atgaagagtt ctatgcacag    840

gaaaccttcg tgcatgttct tccagaaggt gcacagccac aaacccaagc agttcttggc    900

tccaacatgt gccacgtgca ggtagaaatt gatgaggaag caggcaaagt ccttgttacc    960

tccgcaatcg ataacctcac caagggaact gccggcgccg ctgttcagtg catgaactta   1020

agcgttggtt ttgatgaggc agcaggcctg ccacaggtcg gcgtcgcacc ttaa         1074
```

```
<210> SEQ ID NO 33
<211> LENGTH: 357
<212> TYPE: PRT
<213> ORGANISM: Corynebacterium glutamicum

<400> SEQUENCE: 33

Met Ile Met His Asn Val Tyr Gly Val Thr Met Thr Ile Lys Val Ala
1               5                   10                  15

Ile Ala Gly Ala Ser Gly Tyr Ala Gly Gly Glu Ile Leu Arg Leu Leu
            20                  25                  30

Leu Gly His Pro Ala Tyr Ala Ser Gly Glu Leu Glu Ile Gly Ala Leu
        35                  40                  45

Thr Ala Ala Ser Thr Ala Gly Ser Thr Leu Gly Glu Leu Met Pro His
    50                  55                  60

Ile Pro Gln Leu Ala Asp Arg Val Ile Gln Asp Thr Thr Ala Glu Thr
65                  70                  75                  80

Leu Ala Gly His Asp Val Val Phe Leu Gly Leu Pro His Gly Phe Ser
                85                  90                  95

Ala Glu Ile Ala Leu Gln Leu Gly Pro Asp Val Thr Val Ile Asp Cys
            100                 105                 110

Ala Ala Asp Phe Arg Leu Gln Asn Ala Ala Asp Trp Glu Lys Phe Tyr
        115                 120                 125

Gly Ser Glu His Gln Gly Thr Trp Pro Tyr Gly Ile Pro Glu Met Pro
    130                 135                 140

Gly His Arg Glu Ala Leu Arg Gly Ala Lys Arg Val Ala Val Pro Gly
145                 150                 155                 160

Cys Phe Pro Thr Gly Ala Thr Leu Ala Leu Leu Pro Ala Val Gln Ala
                165                 170                 175

Gly Leu Ile Glu Pro Asp Val Ser Val Val Ser Ile Thr Gly Val Ser
            180                 185                 190

Gly Ala Gly Lys Lys Ala Ser Val Ala Leu Leu Gly Ser Glu Thr Met
        195                 200                 205

Gly Ser Leu Lys Ala Tyr Asn Thr Ser Gly Lys His Arg His Thr Pro
    210                 215                 220

Glu Ile Ala Gln Asn Leu Gly Glu Val Ser Asp Lys Pro Val Lys Val
225                 230                 235                 240

Ser Phe Thr Pro Val Leu Ala Pro Leu Pro Arg Gly Ile Leu Thr Thr
                245                 250                 255

Ala Thr Ala Pro Leu Lys Glu Gly Val Thr Ala Glu Gln Ala Arg Ala
            260                 265                 270

Val Tyr Glu Glu Phe Tyr Ala Gln Glu Thr Phe Val His Val Leu Pro
        275                 280                 285

Glu Gly Ala Gln Pro Gln Thr Gln Ala Val Leu Gly Ser Asn Met Cys
    290                 295                 300
```

```
His Val Gln Val Glu Ile Asp Glu Glu Ala Gly Lys Val Leu Val Thr
305                 310                 315                 320

Ser Ala Ile Asp Asn Leu Thr Lys Gly Thr Ala Gly Ala Ala Val Gln
                325                 330                 335

Cys Met Asn Leu Ser Val Gly Phe Asp Glu Ala Ala Gly Leu Pro Gln
            340                 345                 350

Val Gly Val Ala Pro
        355


<210> SEQ ID NO 34
<211> LENGTH: 1167
<212> TYPE: DNA
<213> ORGANISM: Corynebacterium glutamicum

<400> SEQUENCE: 34

atggcagaaa aaggcattac cgcgccgaaa ggcttcgttg cttctgcaac gaccgcgggt      60

attaaagctt ctggcaatcc tgacatggcg ttggtggtta accagggtcc agagttttcc     120

gcagcggccg tgtttacacg taaccgagtt ttcgcagcgc ctgtgaaggt gagccgagag     180

aacgttgctg atggccagat cagggctgtt ttgtacaacg ctggtaatgc taatgcgtgt     240

aatggtctgc agggtgagaa ggatgctcgt gagtctgttt ctcatctagc tcaaaatttg     300

ggcttggagg attccgatat tggtgtgtgt tccactggtc ttattggtga gttgcttccg     360

atggataagc tcaatgcagg tattgatcag ctgaccgctg agggcgcttt gggtgacaat     420

ggtgcagctg ctgccaaggc gatcatgacc actgacacgg tggataagga aaccgtcgtg     480

tttgctgatg gttggactgt cggcggaatg ggcaagggcg tgggcatgat ggcgccgtct     540

cttgccacca tgctggtctg cttgaccact gatgcatccg ttactcagga aatggctcag     600

atcgcgctgg ctaatgctac ggccgttacg tttgacaccc tggatattga tggatcaacc     660

tccaccaatg acaccgtgtt cctgctggca tctggcgcta gcggaatcac cccaactcag     720

gatgaactca acgatgcggt gtacgcagct tgttctgata tcgcagcgaa gcttcaggct     780

gatgcagagg gtgtgaccaa gcgcgttgct gtgacagtgg tgggaaccac caacaacgag     840

caggcgatta atgcggctcg cactgttgct cgtgacaatt tgttcaagtg cgcaatgttt     900

ggatctgatc caaactgggg tcgcgtgttg gctgcagtcg gcatggctga tgctgatatg     960

gaaccagaga agatttctgt gttcttcaat ggtcaagcag tatgccttga ttccactggc    1020

gctcctggtg ctcgtgaggt ggatctttcc ggcgctgaca ttgatgtccg aattgatttg    1080

ggcaccagtg gggaaggcca ggcaacagtt cgaaccactg acctgagctt ctcctacgtg    1140

gagatcaact ccgcgtacag ctcttaa                                        1167


<210> SEQ ID NO 35
<211> LENGTH: 388
<212> TYPE: PRT
<213> ORGANISM: Corynebacterium glutamicum

<400> SEQUENCE: 35

Met Ala Glu Lys Gly Ile Thr Ala Pro Lys Gly Phe Val Ala Ser Ala
1               5                   10                  15

Thr Thr Ala Gly Ile Lys Ala Ser Gly Asn Pro Asp Met Ala Leu Val
            20                  25                  30

Val Asn Gln Gly Pro Glu Phe Ser Ala Ala Ala Val Phe Thr Arg Asn
        35                  40                  45

Arg Val Phe Ala Ala Pro Val Lys Val Ser Arg Glu Asn Val Ala Asp
    50                  55                  60
```

```
Gly Gln Ile Arg Ala Val Leu Tyr Asn Ala Gly Asn Ala Asn Ala Cys
65                  70                  75                  80

Asn Gly Leu Gln Gly Glu Lys Asp Ala Arg Glu Ser Val Ser His Leu
                85                  90                  95

Ala Gln Asn Leu Gly Leu Glu Asp Ser Asp Ile Gly Val Cys Ser Thr
            100                 105                 110

Gly Leu Ile Gly Glu Leu Leu Pro Met Asp Lys Leu Asn Ala Gly Ile
        115                 120                 125

Asp Gln Leu Thr Ala Glu Gly Ala Leu Gly Asp Asn Gly Ala Ala Ala
    130                 135                 140

Ala Lys Ala Ile Met Thr Thr Asp Thr Val Asp Lys Glu Thr Val Val
145                 150                 155                 160

Phe Ala Asp Gly Trp Thr Val Gly Gly Met Gly Lys Gly Val Gly Met
                165                 170                 175

Met Ala Pro Ser Leu Ala Thr Met Leu Val Cys Leu Thr Thr Asp Ala
            180                 185                 190

Ser Val Thr Gln Glu Met Ala Gln Ile Ala Leu Ala Asn Ala Thr Ala
        195                 200                 205

Val Thr Phe Asp Thr Leu Asp Ile Asp Gly Ser Thr Ser Thr Asn Asp
    210                 215                 220

Thr Val Phe Leu Leu Ala Ser Gly Ala Ser Gly Ile Thr Pro Thr Gln
225                 230                 235                 240

Asp Glu Leu Asn Asp Ala Val Tyr Ala Ala Cys Ser Asp Ile Ala Ala
                245                 250                 255

Lys Leu Gln Ala Asp Ala Glu Gly Val Thr Lys Arg Val Ala Val Thr
            260                 265                 270

Val Val Gly Thr Thr Asn Asn Glu Gln Ala Ile Asn Ala Ala Arg Thr
        275                 280                 285

Val Ala Arg Asp Asn Leu Phe Lys Cys Ala Met Phe Gly Ser Asp Pro
    290                 295                 300

Asn Trp Gly Arg Val Leu Ala Ala Val Gly Met Ala Asp Ala Asp Met
305                 310                 315                 320

Glu Pro Glu Lys Ile Ser Val Phe Phe Asn Gly Gln Ala Val Cys Leu
                325                 330                 335

Asp Ser Thr Gly Ala Pro Gly Ala Arg Glu Val Asp Leu Ser Gly Ala
            340                 345                 350

Asp Ile Asp Val Arg Ile Asp Leu Gly Thr Ser Gly Glu Gly Gln Ala
        355                 360                 365

Thr Val Arg Thr Thr Asp Leu Ser Phe Ser Tyr Val Glu Ile Asn Ser
    370                 375                 380

Ala Tyr Ser Ser
385
```

<210> SEQ ID NO 36
<211> LENGTH: 954
<212> TYPE: DNA
<213> ORGANISM: Corynebacterium glutamicum

<400> SEQUENCE: 36

```
atgaatgact tgatcaaaga tttaggctct gaggtgcgcg caaatgtcct cgctgaggcg      60

ttgccatggt tgcagcactt ccgcgacaag attgttgtcg tgaaatatgg cggaaacgcc     120

atggtggatg atgatctcaa ggctgctttt gctgccgaca tggtcttctt gcgcaccgtg     180

ggcgcaaaac cagtggtggt gcacggtggt ggacctcaga tttctgagat gctaaaccgt     240
```

```
gtgggtctcc agggcgagtt caagggtggt ttccgtgtga ccactcctga ggtcatggac    300

attgtgcgca tggtgctctt tggtcaggtc ggtcgcgatt tagttggttt gatcaactct    360

catggccctt acgctgtggg aacctccggt gaggatgccg gcctgtttac cgcgcagaag    420

cgcatggtca acatcgatgg cgtacccact gatattggtt tggtcggaga catcattaat    480

gtcgatgcct cttccttgat ggatatcatc gaggccggtc gcattcctgt ggtctctacg    540

attgctccag gcgaagacgg ccagatttac aacattaacg ccgataccgc agcaggtgct    600

ttggctgcag cgattggtgc agaacgcctg ctggttctca ccaatgtgga aggtctgtac    660

accgattggc ctgataagag ctcactggtg tccaagatca aggccaccga gctggaggcc    720

attcttccgg gacttgattc cggcatgatt ccaaagatgg agtcttgctt gaacgcggtg    780

cgtgggggag taagcgctgc tcatgtcatt gacggccgca tcgcgcactc ggtgttgctg    840

gagcttttga ccatgggtgg aattggcacg atggtgctgc cggatgtttt tgatcgggag    900

aattatcctg aaggcaccgt ttttagaaaa gacgacaagg atggggaact gtaa          954
```

<210> SEQ ID NO 37
<211> LENGTH: 317
<212> TYPE: PRT
<213> ORGANISM: Corynebacterium glutamicum

<400> SEQUENCE: 37

```
Met Asn Asp Leu Ile Lys Asp Leu Gly Ser Glu Val Arg Ala Asn Val
1               5                   10                  15

Leu Ala Glu Ala Leu Pro Trp Leu Gln His Phe Arg Asp Lys Ile Val
            20                  25                  30

Val Val Lys Tyr Gly Gly Asn Ala Met Val Asp Asp Asp Leu Lys Ala
        35                  40                  45

Ala Phe Ala Ala Asp Met Val Phe Leu Arg Thr Val Gly Ala Lys Pro
    50                  55                  60

Val Val Val His Gly Gly Gly Pro Gln Ile Ser Glu Met Leu Asn Arg
65                  70                  75                  80

Val Gly Leu Gln Gly Glu Phe Lys Gly Gly Phe Arg Val Thr Thr Pro
                85                  90                  95

Glu Val Met Asp Ile Val Arg Met Val Leu Phe Gly Gln Val Gly Arg
            100                 105                 110

Asp Leu Val Gly Leu Ile Asn Ser His Gly Pro Tyr Ala Val Gly Thr
        115                 120                 125

Ser Gly Glu Asp Ala Gly Leu Phe Thr Ala Gln Lys Arg Met Val Asn
    130                 135                 140

Ile Asp Gly Val Pro Thr Asp Ile Gly Leu Val Gly Asp Ile Ile Asn
145                 150                 155                 160

Val Asp Ala Ser Ser Leu Met Asp Ile Ile Glu Ala Gly Arg Ile Pro
                165                 170                 175

Val Val Ser Thr Ile Ala Pro Gly Glu Asp Gly Gln Ile Tyr Asn Ile
            180                 185                 190

Asn Ala Asp Thr Ala Ala Gly Ala Leu Ala Ala Ala Ile Gly Ala Glu
        195                 200                 205

Arg Leu Leu Val Leu Thr Asn Val Glu Gly Leu Tyr Thr Asp Trp Pro
    210                 215                 220

Asp Lys Ser Ser Leu Val Ser Lys Ile Lys Ala Thr Glu Leu Glu Ala
225                 230                 235                 240

Ile Leu Pro Gly Leu Asp Ser Gly Met Ile Pro Lys Met Glu Ser Cys
```

-continued

```
                245                 250                 255

Leu Asn Ala Val Arg Gly Gly Val Ser Ala Ala His Val Ile Asp Gly
            260                 265                 270

Arg Ile Ala His Ser Val Leu Leu Glu Leu Leu Thr Met Gly Gly Ile
        275                 280                 285

Gly Thr Met Val Leu Pro Asp Val Phe Asp Arg Glu Asn Tyr Pro Glu
    290                 295                 300

Gly Thr Val Phe Arg Lys Asp Asp Lys Asp Gly Glu Leu
305                 310                 315


<210> SEQ ID NO 38
<211> LENGTH: 1176
<212> TYPE: DNA
<213> ORGANISM: Corynebacterium glutamicum

<400> SEQUENCE: 38

atgagcacgc tggaaacttg gccacaggtc attattaata cgtacggcac ccccaccagtt     60

gagctggtgt ccggcaaggg cgcaaccgtc actgatgacc agggcaatgt ctacatcgac    120

ttgctcgcgg gcatcgcagt caacgcgttg ggccacgccc acccggcgat catcgaggcg    180

gtcaccaacc agatcggcca acttggtcac gtctcaaact tgttcgcatc caggcccgtc    240

gtcgaggtcg ccgaggagct catcaagcgt ttttcgcttg acgacgccac cctcgccgcg    300

caaacccggg ttttcttctg caactcgggc gccgaagcaa acgaggctgc tttcaagatt    360

gcacgcttga ctggtcgttc ccggattctg gctgcagttc atggtttcca cggccgcacc    420

atgggttccc tcgcgctgac tggccagcca gacaagcgtg aagcgttcct gccaatgcca    480

agcggtgtgg agttctaccc ttacggcgac accgattact tgcgcaaaat ggtagaaacc    540

aacccaacgg atgtggctgc tatcttcctc gagccaatcc agggtgaaac gggcgttgtt    600

ccagcacctg aaggattcct caaggcagtg cgcgagctgt gcgatgagta cggcatcttg    660

atgatcaccg atgaagtcca gactggcgtt ggccgtaccg gcgatttctt tgcacatcag    720

cacgatggcg ttgttcccga tgtggtgacc atggccaagg gacttggcgg cggtcttccc    780

atcggtgctt gtttggccac tggccgtgca gctgaattga tgaccccagg caagcacggc    840

accactttcg gtggcaaccc agttgcttgt gcagctgcca aggcagtgct gtctgttgtc    900

gatgacgctt tctgcgcaga agttgcccgc aagggcgagc tgttcaagga acttcttgcc    960

aaggttgacg gcgttgtaga cgtccgtggc aggggcttga tgttgggcgt ggtgctggag   1020

cgcgacgtcg caaagcaagc tgttcttgat ggttttaagc acggcgttat tttgaatgca   1080

ccggcggaca acattatccg tttgaccccg ccgctggtga tcaccgacga agaaatcgca   1140

gacgcagtca aggctattgc cgagacaatc gcataa                             1176


<210> SEQ ID NO 39
<211> LENGTH: 391
<212> TYPE: PRT
<213> ORGANISM: Corynebacterium glutamicum

<400> SEQUENCE: 39

Met Ser Thr Leu Glu Thr Trp Pro Gln Val Ile Ile Asn Thr Tyr Gly
1               5                   10                  15

Thr Pro Pro Val Glu Leu Val Ser Gly Lys Gly Ala Thr Val Thr Asp
            20                  25                  30

Asp Gln Gly Asn Val Tyr Ile Asp Leu Leu Ala Gly Ile Ala Val Asn
        35                  40                  45
```

-continued

```
Ala Leu Gly His Ala His Pro Ala Ile Ile Glu Ala Val Thr Asn Gln
    50                  55                  60

Ile Gly Gln Leu Gly His Val Ser Asn Leu Phe Ala Ser Arg Pro Val
65                  70                  75                  80

Val Glu Val Ala Glu Glu Leu Ile Lys Arg Phe Ser Leu Asp Asp Ala
                85                  90                  95

Thr Leu Ala Ala Gln Thr Arg Val Phe Phe Cys Asn Ser Gly Ala Glu
            100                 105                 110

Ala Asn Glu Ala Ala Phe Lys Ile Ala Arg Leu Thr Gly Arg Ser Arg
        115                 120                 125

Ile Leu Ala Ala Val His Gly Phe His Gly Arg Thr Met Gly Ser Leu
    130                 135                 140

Ala Leu Thr Gly Gln Pro Asp Lys Arg Glu Ala Phe Leu Pro Met Pro
145                 150                 155                 160

Ser Gly Val Glu Phe Tyr Pro Tyr Gly Asp Thr Asp Tyr Leu Arg Lys
                165                 170                 175

Met Val Glu Thr Asn Pro Thr Asp Val Ala Ala Ile Phe Leu Glu Pro
            180                 185                 190

Ile Gln Gly Glu Thr Gly Val Val Pro Ala Pro Glu Gly Phe Leu Lys
        195                 200                 205

Ala Val Arg Glu Leu Cys Asp Glu Tyr Gly Ile Leu Met Ile Thr Asp
    210                 215                 220

Glu Val Gln Thr Gly Val Gly Arg Thr Gly Asp Phe Phe Ala His Gln
225                 230                 235                 240

His Asp Gly Val Val Pro Asp Val Val Thr Met Ala Lys Gly Leu Gly
                245                 250                 255

Gly Gly Leu Pro Ile Gly Ala Cys Leu Ala Thr Gly Arg Ala Ala Glu
            260                 265                 270

Leu Met Thr Pro Gly Lys His Gly Thr Thr Phe Gly Gly Asn Pro Val
        275                 280                 285

Ala Cys Ala Ala Ala Lys Ala Val Leu Ser Val Val Asp Asp Ala Phe
    290                 295                 300

Cys Ala Glu Val Ala Arg Lys Gly Glu Leu Phe Lys Glu Leu Leu Ala
305                 310                 315                 320

Lys Val Asp Gly Val Val Asp Val Arg Gly Arg Gly Leu Met Leu Gly
                325                 330                 335

Val Val Leu Glu Arg Asp Val Ala Lys Gln Ala Val Leu Asp Gly Phe
            340                 345                 350

Lys His Gly Val Ile Leu Asn Ala Pro Ala Asp Asn Ile Ile Arg Leu
        355                 360                 365

Thr Pro Pro Leu Val Ile Thr Asp Glu Glu Ile Ala Asp Ala Val Lys
    370                 375                 380

Ala Ile Ala Glu Thr Ile Ala
385                 390
```

<210> SEQ ID NO 40
<211> LENGTH: 2136
<212> TYPE: DNA
<213> ORGANISM: Escherichia coli

<400> SEQUENCE: 40

```
atgaaatcaa tgaatattgc cgccagtagt gaactggtat cccgactttc ttctcatcgt      60

cgcgtggtgg cgttgggaga tactgatttt acggacgtcg cggcagtcgt cattaccgct     120

gcggatagtc gcagtggcat tcttgcgttg cttaagcgca ccggttttca tctaccggtg     180
```

```
tttttgtatt ccgaacatgc tgttgaatta cctgcgggcg ttacggcggt aatcaacggc    240
aacgagcagc agtggctgga gctggaatcc gcagcctgtc agtatgaaga gaatttgctg    300
ccaccgtttt atgacacgct gacgcagtac gttgagatgg gcaacagcac ctttgcttgc    360
cctggacatc aacatggtgc gttttttaaa aagcatcctg ccggacgcca tttttacgat    420
ttctttggtg agaacgtctt tcgcgccgat atgtgtaacg ctgacgtaaa attgggcgat    480
ctgcttattc atgaaggatc ggcgaaagat gcgcagaaat tcgcagccaa agtctttcat    540
gccgataaaa cctattttgt gctgaacggc acatcggcag cgaataaagt ggtgacgaat    600
gcgctgttaa cgcgtggcga tctggtgctc ttcgaccgta acaaccataa gtcgaatcat    660
cacggcgcgc tgattcaggc gggggcgacg ccggtctatc tggaagcttc acgcaacccg    720
tttggtttca ttggcggtat tgatgcgcac tgttttaatg aagagtatct gcgccagcaa    780
attcgcgacg ttgcgccaga aaaagccgac ctgccgcgcc cgtatcgcct ggcgattatt    840
cagctgggaa cctatgacgg cactgtctat aacgcccgtc aggtgatcga taccgttggg    900
catctgtgtg attacattct gtttgattcc gcgtgggtcg gttatgaaca atttatcccg    960
atgatggcgg atagctcgcc gctgctgtta gaacttaacg aaaacgatcc ggggatcttt   1020
gtgactcagt cggtgcacaa acagcaggcg ggattctcac agacgtcgca gatccataaa   1080
aaagataacc atatccgcgg acaggcgcgt tttgcccgc ataagcggtt gaataacgcc   1140
tttatgctcc atgcttctac cagccctttc tatccgctgt ttgctgcact ggatgttaac   1200
gccaaaattc atgaagggga gagtgggcgt cggctgtggg ctgagtgtgt tgagataggg   1260
attgaagcgc gcaaggctat tcttgcgcgc tgtaagctgt tccgcccgtt tatcccgccc   1320
gttgttgatg gcaaattgtg gcaggattat ccgacatcag tgttagccag cgaccgccgt   1380
tttttcagtt ttgagccggg ggcgaagtgg cacggctttg aaggatatgc cgcggatcag   1440
tattttgttg atccgtgcaa gctgttactc actacaccag gtatcgatgc cgaaaccggc   1500
gaatatagcg actttggcgt tccggcgacg attctggcgc actatctgcg tgagaacggc   1560
attgtgccgg agaagtgcga tctcaactcc attctgtttt tattaactcc ggcggaaagc   1620
cacgagaagc tggcacaact ggtggcgatg ctggcgcaat ttgaacagca tattgaggat   1680
gactcgccgc tggttgaggt gttgccgagc gtttataaca agtatccggt gcgctatcgc   1740
gactacaccc tgcgccagtt gtgtcaggag atgcacgatc tgtatgtcag tttcgacgtc   1800
aaagacctac aaaaagcgat gttccgccag cagagtttcc cgtcagtggt gatgaacccc   1860
caggatgcgc atagcgctta tattcgcggt gacgtggagt tggtgcggat tcgtgatgcc   1920
gaagggcgaa ttgcggcaga aggggcgttg ccttatccac ctggcgtgct ttgcgtggta   1980
cccggggaag tctggggtgg ggcggttcaa cgttatttcc ttgcactgga agaaggggtg   2040
aatttgttgc cgggattttc gccggagctg caaggtgttt atagcgaaac cgatgcggat   2100
ggcgtgaaac ggttgtacgg ttatgtgttg aagtaa                             2136
```

<210> SEQ ID NO 41
<211> LENGTH: 711
<212> TYPE: PRT
<213> ORGANISM: Escherichia coli

<400> SEQUENCE: 41

```
Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
```

```
            20                  25                  30

Val Ala Ala Val Val Ile Thr Ala Ala Asp Ser Arg Ser Gly Ile Leu
        35                  40                  45

Ala Leu Leu Lys Arg Thr Gly Phe His Leu Pro Val Phe Leu Tyr Ser
    50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Ile His Glu Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190

Ala Ala Asn Lys Val Val Thr Asn Ala Leu Leu Thr Arg Gly Asp Leu
        195                 200                 205

Val Leu Phe Asp Arg Asn Asn His Lys Ser Asn His His Gly Ala Leu
    210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
        275                 280                 285

Val Tyr Asn Ala Arg Gln Val Ile Asp Thr Val Gly His Leu Cys Asp
    290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Gln Ala Gly Phe
            340                 345                 350

Ser Gln Thr Ser Gln Ile His Lys Lys Asp Asn His Ile Arg Gly Gln
        355                 360                 365

Ala Arg Phe Cys Pro His Lys Arg Leu Asn Asn Ala Phe Met Leu His
    370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
            420                 425                 430

Leu Phe Arg Pro Phe Ile Pro Pro Val Val Asp Gly Lys Leu Trp Gln
        435                 440                 445
```

```
Asp Tyr Pro Thr Ser Val Leu Ala Ser Asp Arg Arg Phe Phe Ser Phe
    450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
            500                 505                 510

Ala His Tyr Leu Arg Glu Asn Gly Ile Val Pro Glu Lys Cys Asp Leu
        515                 520                 525

Asn Ser Ile Leu Phe Leu Leu Thr Pro Ala Glu Ser His Glu Lys Leu
    530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
        595                 600                 605

Arg Gln Gln Ser Phe Pro Ser Val Val Met Asn Pro Gln Asp Ala His
    610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
                645                 650                 655

Leu Cys Val Val Pro Gly Glu Val Trp Gly Gly Ala Val Gln Arg Tyr
            660                 665                 670

Phe Leu Ala Leu Glu Glu Gly Val Asn Leu Leu Pro Gly Phe Ser Pro
        675                 680                 685

Glu Leu Gln Gly Val Tyr Ser Glu Thr Asp Ala Asp Gly Val Lys Arg
    690                 695                 700

Leu Tyr Gly Tyr Val Leu Lys
705                 710


<210> SEQ ID NO 42
<211> LENGTH: 318
<212> TYPE: DNA
<213> ORGANISM: Artificial Sequence
<220> FEATURE:
<223> OTHER INFORMATION: CJ7 promoter

<400> SEQUENCE: 42

agaaacatcc cagcgctact aatagggagc gttgaccttc cttccacgga ccggtaatcg      60

gagtgcctaa aaccgcatgc ggcttaggct ccaagatagg ttctgcgcgg ccgggtaatg     120

catcttcttt agcaacaagt tgaggggtag gtgcaaataa gaacgacata gaaatcgtct     180

cctttctgtt tttaatcaac atacaccacc acctaaaaat tccccgacca gcaagttcac     240

agtattcggg cacaatatcg ttgccaaaat attgtttcgg aatatcatgg gatacgtacc     300

caacgaaagg aaacactc                                                   318
```